United States Patent
Hong et al.

(10) Patent No.: US 11,016,388 B2
(45) Date of Patent: May 25, 2021

(54) OVERCOAT COMPOSITIONS AND METHODS FOR PHOTOLITHOGRAPHY

(71) Applicant: Rohm and Haas Electronic Materials Korea Ltd., Cheonan, Chungcheongnam-Do (KR)

(72) Inventors: Chang-Young Hong, Chungcheongnam-Do (KR); Eui Hyun Ryu, Chungcheongnam-Do (KR); Min-Kyung Jang, Chungcheongnam-Do (KR); Dong-Yong Kim, Chungcheongnam-Do (KR)

(73) Assignee: Rohm and Haas Electronic Materials Korea Ltd., Chungcheongnam-do (KR)

( * ) Notice: Subject to any disclaimer, the term of this patent is extended or adjusted under 35 U.S.C. 154(b) by 0 days.

(21) Appl. No.: 15/281,700

(22) Filed: Sep. 30, 2016

(65) Prior Publication Data

US 2017/0090287 A1  Mar. 30, 2017

Related U.S. Application Data

(60) Provisional application No. 62/235,384, filed on Sep. 30, 2015.

(51) Int. Cl.
| | |
|---|---|
| *G03F 7/004* | (2006.01) |
| *G03F 7/30* | (2006.01) |
| *C08F 222/22* | (2006.01) |
| *C08F 222/24* | (2006.01) |
| *G03F 7/11* | (2006.01) |
| *G03F 7/32* | (2006.01) |
| *C08F 220/38* | (2006.01) |
| *C07C 271/12* | (2006.01) |
| *C07D 211/48* | (2006.01) |
| *C08F 220/16* | (2006.01) |
| *C08F 220/28* | (2006.01) |
| *C09D 133/14* | (2006.01) |
| *G03F 7/16* | (2006.01) |
| *G03F 7/20* | (2006.01) |
| *G03F 7/40* | (2006.01) |

(52) U.S. Cl.
CPC .............. *G03F 7/11* (2013.01); *C07C 271/12* (2013.01); *C07D 211/48* (2013.01); *C08F 220/16* (2013.01); *C08F 220/28* (2013.01); *C08F 220/38* (2013.01); *C08F 222/22* (2013.01); *C08F 222/24* (2013.01); *C09D 133/14* (2013.01); *G03F 7/0045* (2013.01); *G03F 7/162* (2013.01); *G03F 7/2041* (2013.01); *G03F 7/325* (2013.01); *G03F 7/40* (2013.01); *C08F 2220/283* (2013.01)

(58) Field of Classification Search
CPC . G03F 7/0392; G03F 7/11; G03F 7/30; C08F 222/22; C08F 222/24; C08F 220/38
USPC ............ 430/273.1, 270.1, 910; 526/288, 301
See application file for complete search history.

(56) References Cited

U.S. PATENT DOCUMENTS

| | | | |
|---|---|---|---|
| 9,091,933 B2 * | 7/2015 | Kobayashi | C08F 226/06 |
| 2006/0172149 A1 | 8/2006 | Ahn et al. | |
| 2007/0190451 A1 | 8/2007 | Ishii et al. | |
| 2011/0236831 A1 | 9/2011 | Hasegawa et al. | |
| 2011/0305979 A1 | 12/2011 | Harada et al. | |
| 2012/0183903 A1 | 7/2012 | Hatakeyama et al. | |
| 2012/0183904 A1 * | 7/2012 | Sagehashi | G03F 7/0045 430/285.1 |
| 2013/0130183 A1 * | 5/2013 | Kobayashi | C08F 228/06 430/325 |
| 2013/0177853 A1 | 7/2013 | Shimizu et al. | |
| 2013/0344436 A1 | 12/2013 | Nakamura et al. | |
| 2014/0038102 A1 | 2/2014 | Park et al. | |
| 2015/0147697 A1 * | 5/2015 | Hatakeyama | C08F 12/20 430/285.1 |

FOREIGN PATENT DOCUMENTS

| | | |
|---|---|---|
| EP | 1702962 B1 | 12/2008 |
| JP | H11337722 A | 12/1999 |
| JP | 2007-316448 A | 12/2007 |
| JP | 2010-111461 A | 5/2010 |
| JP | 20115442 A | 1/2011 |
| JP | 2013045055 A | 3/2013 |
| JP | 2013064971 A | 4/2013 |
| KR | 2010068083 A | 6/2010 |
| TW | 2013/00954 A | 1/2013 |

OTHER PUBLICATIONS

English language summary of Office Action dated Dec. 20, 2018 in counterpart Japan application 2016/189423.
English language summary of first Office Action issued in counterpart China Application CN 201610851432.2.
English language summary of Office Action dated Mar. 7, 2018 issued in counterpart KR Application 10-2016-0124760.

* cited by examiner

*Primary Examiner* — John S Chu
(74) *Attorney, Agent, or Firm* — Mintz Levin Cohn Ferris Glovsky and Popeo, P.C.; Peter F. Corless

(57) ABSTRACT

Topcoat compositions are provided that are suitably applied above a photoresist composition. Preferred topcoat compositions comprise a first polymer comprising first units comprising a reactive nitrogen-containing moiety spaced from the polymer backbone, wherein the nitrogen-containing moiety produces a basic cleavage product during lithographic processing of the photoresist composition.

8 Claims, No Drawings

OVERCOAT COMPOSITIONS AND METHODS FOR PHOTOLITHOGRAPHY

CROSS-REFERENCE TO RELATED APPLICATION

This application claims priority to U.S. Provisional Application No. 62/235,384, filed Sep. 30, 2015. The contents of the foregoing application is incorporated herein by reference in its entirety.

BACKGROUND

The invention relates to overcoat or topcoat layer compositions that may be applied above a photoresist composition. The invention is particularly useful as a topcoat layer in an immersion lithography process for the formation of semiconductor devices.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

One approach to achieving nanometer (nm)-scale feature sizes in semiconductor devices is to use shorter wavelengths of light. However, the difficulty in finding materials that are transparent below 193 nm has led to the immersion lithography process to increase the numerical aperture of the lens by use of a liquid to focus more light into the film. Immersion lithography employs a relatively high refractive index fluid between the last surface of an imaging device (e.g., KrF or ArF light source) and the first surface on the substrate, for example, a semiconductor wafer.

In immersion lithography, direct contact between the immersion fluid and photoresist layer can result in leaching of components of the photoresist into the immersion fluid. This leaching can cause contamination of the optical lens and bring about a change in the effective refractive index and transmission properties of the immersion fluid. In an effort to ameliorate this problem, use of a topcoat layer over the photoresist layer as a barrier between the immersion fluid and underlying photoresist layer has been proposed. The use of topcoat layers in immersion lithography, however, presents various challenges. Topcoat layers can affect, for example, the process window, critical dimension (CD) variation and resist profile depending on characteristics such as topcoat refractive index, thickness, acidity, chemical interaction with the resist and soaking time. In addition, use of a topcoat layer can negatively impact device yield due, for example, to micro-bridging defects which prevent proper resist pattern formation.

To improve performance of topcoat materials, the use of self-segregating topcoat compositions to form a graded topcoat layer has been proposed, for example, in *Self-segregating Materials for Immersion Lithography*, Daniel P. Sanders et al, Advances in Resist Materials and Processing Technology XXV, Proceedings of the SPIE, Vol. 6923, pp. 692309-1-692309-12 (2008). See also US20120264053, A self-segregated topcoat would theoretically allow for a tailored material having desired properties at both the immersion fluid and photoresist interfaces, for example, a high water receding contact angle at the immersion fluid interface and good developer solubility at the photoresist interface.

Electronic device manufacturers continually seek increased resolution of a patterned photoresist image. It would be desirable to have new topcoat compositions that could provide enhanced imaging capabilities.

SUMMARY

We now provide new topcoat compositions and methods for use of such compositions, including use of the compositions together with an underlying photoresist composition in immersion lithography processes.

In one aspect, preferred topcoat compositions comprise a first polymer comprising first units comprising a reactive nitrogen-containing moiety spaced from the polymer backbone, wherein the nitrogen-containing moiety produces a basic cleavage product during lithographic processing of the photoresist composition.

As referred to herein, a basic cleavage product includes moieties that include one or more nitrogen atoms. A basic cleavage product can be produced as a basic moiety (e.g. moiety with one or more nitrogen atoms) is cleaved (i.e. covalent bond breakage) from the first polymer through reaction of an acid-labile group in the optional presence of an acid generator and optional thermal treatment (e.g. post-exposure bake).

The reactive nitrogen-containing moiety can be spaced from the polymer backbone by any of a number of groups including for example alkyl (alkylene); a ring group comprising carbon atoms; and/or hetero atoms such as oxygen or optionally substituted sulfur (e.g. S(O), S(O)$_2$), in a chain that comprises 1 or more atoms (including carbon atoms), generally 1, 2, 3, 4, 5, 6, 7, 8, 9 or 10 atoms (including carbon atoms), interposed between the polymer backbone and the reactive nitrogen-containing moiety.

As understood, the term polymer backbone refers to the series of covalently bonded atoms that together create the continuous linear chain of the polymer. In poly(acrylate) or poly(alkylacrylate) (such as poly(methacrylate)) resins, the reactive nitrogen-containing moiety can be spaced from the polymerized acrylate carboxy (—CH$_2$—CH(COO—)—) moiety or alkylacrylate carboxy (—CH$_2$—C(alkyl)(COO—)—) moiety by 1 or more atoms (including carbon atoms), generally 1, 2, 3, 4, 5, 6, 7, 8, 9 or 10 atoms (including carbon atoms).

In certain preferred aspects, 1, 2, 3, 4 or 5 optionally substituted carbon atoms (spacer group) may be interposed between a polymerized acrylate or alkylacrylate (such as methacrylate) polymer backbone moiety and a reactive nitrogen-containing moiety such as carbamate (e.g. spacer group interposed between and linked to 1) acrylate or alkylacrylate moiety and 2) —O(C=O)—N< or >N(=O)O—). Such preferred spacer groups may be part of a non-cyclic chain or a cyclic group where the cyclic group may or may not contain a nitrogen (e.g. a nitrogen of a carbamate group) as a ring member. Such preferred spacer groups also may be optionally substituted, for example one or more of the interposed carbon atoms of the spacer group may be substituted by one or more alkyl groups such as C$_{1-12}$alkyl including methyl, or a cyclic alkyl such as cyclohexyl, or by another ring member carbon.

An acid-labile moiety such as an acid-labile ester or acetal group also may be preferably interposed between a polymer backbone and the reactive nitrogen-containing moiety. For instance, in one preferred aspect, a photoacid-labile ester (particularly, ester substituted with quaternary carbon, i.e. —C(=O)OY where Y is a quaternary carbon) is interposed between the polymer backbone and a reactive nitrogen-containing moiety.

In certain embodiments, the topcoat compositions also suitably comprise one or more acid generators, such as one or more photoacid generators and/or one or more thermal acid generators.

Preferably, the first polymer further comprises second units each comprising 1) a reactive nitrogen-containing moiety and 2) an acid-labile group. Also preferably, the nitrogen-containing moiety is spaced from the polymer by optionally substituted alkylene, optionally substituted carbon alicyclic, optionally substituted heteroalicyclic, optionally substituted carbocyclic aryl or optionally substituted heteroaryl.

In additional preferred aspects, the first polymer further comprises third units that 1) comprise one or more hydrophobic groups and 2) are distinct from both of the first and second units.

In certain preferred aspects, the nitrogen-containing moiety is a protected amine. For instance, the nitrogen-containing moiety is suitably a carbamate or sulfamate.

In an additional preferred aspect, topcoat compositions are provided that comprise (a) a polymer comprising: units comprising 1) a reactive nitrogen-containing moiety spaced from the polymer backbone, wherein the nitrogen-containing moiety produces a basic cleavage product during lithographic processing of the topcoat and 2) an acid-labile group. In certain embodiments, such topcoat compositions also suitably comprise one or more acid generators, such as one or more photoacid generators and/or one or more thermal acid generators.

In certain preferred aspects, the present topcoat may comprise an additional polymer (second polymer). The second polymer suitably may comprise acid-labile group. As further discussed below, in certain embodiments, the first and second polymers may have differing surface energies.

In certain preferred aspects, the first polymer may further comprise third units that (1) comprise one or more hydrophobic groups and (2) are distinct from the first and second units. Suitably, the one or more hydrophobic groups of the second units and, if present third units, each comprises 3, 4, 5, 6, 7, 8 or more carbon atoms.

Preferably, prior to lithographic processing, the nitrogen-containing moiety of the first polymer is a protected amine which can be can be deprotected in the presence of acid produced during lithographic processing. For instance, the acid may be generated from one or more photoacid generators and/or thermal acid generators present in photoresist composition overlying the topcoat composition. Such acid generated in the underlying photoresist layer can migrate to the overlying topcoat composition layer. Alternatively, in embodiments as discussed above where a topcoat composition comprises one or more photoacid generators and/or thermal acid generators present in the topcoat composition that generate acid during exposure and/or post-exposure bake processing steps of a coating layer of the topcoat composition.

Typically, such a deprotected nitrogen will be significantly more basic than the same nitrogen in protected form prior to lithographic processing. For instance, the pKa differential between 1) the nitrogen-containing moiety prior to lithographic processing and 2) the nitrogen-containing moiety upon deprotection in the presence of acid during lithographic processing suitably may be from 1 to 2, 3, 4, 5, 6, 7, 8, 9, 10, 11, 12, 13 or 14 or more.

In certain additional preferred aspects, in a first polymer of a topcoat composition, the (i) units that comprise a nitrogen-containing moiety also further comprise a hydrophobic group. For instance, the acid-labile moiety of the protected nitrogen moiety may comprise a hydrophobic group such as an optionally substituted straight, branched or cyclic alkyl having 3, 4, 5, 6, 7, 8, 9, 10 or more carbons, e.g. isopropyl, t-butyl, sec-pentyl, adamantyl including methyladamntyl and 1-ethylcyclopentyl.

Particularly preferred first polymers may be provided by polymerization of one or more monomers of the following Formula (I):

$$X_1-R_1-X_2-R_2-X_3 \quad (I)$$

wherein $X_1$ is a polymerizable functional group such as an acrylate or alkylacrylate (e.g. methacrylate); $R_1$ may be an optionally substituted linear, branched or cyclic aliphatic group (including alkyl) having 1 to 30 carbon atoms or an optionally substituted aromatic group such as optionally substituted phenyl or naphthyl; $X_2$ is a basic moiety such as a nitrogen and may be a component of or be taken together with $R_1$ (e.g. $R_1$ and $X_2$ may combine to form a piperdinyl moiety); $R_2$ is an acid labile group such as carbamate or sulfamate; and $X_3$ may be an optionally substituted linear, branched or cyclic aliphatic group (including alkyl) having 1 to 30 carbon atoms or an optionally substituted aromatic group such as optionally substituted phenyl or naphthyl. $R_2$ and $R_3$ may together form an acid labile group e.g. $R_2$ can be —C(=O)O— and $X_3$ can be comprise a quaternary carbon such as t-butyl (thus, $R_2$ and $X_3$ would be —C(=O)OC(CH$_3$)$_3$).

According to a further aspect, coated substrates are provided. The coated substrates comprise a substrate and a layer of a topcoat composition of the invention over a surface of the substrate. In particular aspects, the coated substrates comprise a substrate, a layer of a photoresist composition over a surface of the substrate, and a layer of a topcoat composition of the invention above the photoresist composition layer.

According to a yet further aspect, methods of forming a photolithographic pattern are provided. The methods suitably comprise: (a) providing a substrate comprising one or more layers to be patterned over a surface of the substrate; (b) applying a layer of a photoresist composition over the one or more layers to be patterned; (c) applying a layer of a topcoat composition of the invention over or above the photoresist composition layer; (d) patternwise exposing both the topcoat composition layer and the photoresist composition layer to activating radiation; and (e) applying a developer to the imaged, coated substrate to thereby produce a resist relief image. Suitably, the exposed photoresist composition and topcoat composition layers are thermally treated in a post-exposure bake process prior to development. In preferred aspects, an acid-labile group of a nitrogen-containing moiety of a first polymer of the topcoat composition will undergo reaction during the exposing and a post-exposure, pre-developing thermal treatment to provide an amine linked to the first polymer. The patternwise exposing can be conducted by immersion lithography or, alternatively, using dry exposure techniques. In certain aspects, implant and EUV lithography processes are also preferred.

In a preferred aspect, unexposed portions of the topcoat and photoresist layers are removed by the developer, leaving a photoresist pattern over the one or more layers to be patterned. As discussed, topcoat compositions of the invention are particularly suitable for use in negative tone development processes.

Electronic devices formed by the disclosed methods are also provided, including devices formed by the disclosed negative tone development processes.

References herein to pKa values of nitrogen-containing groups or other groups designate values determined by Taft parameter analysis, as such analysis is known in this field and described in J. Cameron et al., "Structural Effects of Photoacid Generators on Deep UV Resist Performance," Society of Plastic Engineers, Inc. Proceedings., "Photopolymers, Principles, Processes and Materials, 11$^{th}$ International Conference, pp. 120-139 (1997); and J. P. Gutthrie, Can. J Chem., 56:2342-2354 (1978).

As used herein, the articles "a" and "an" are inclusive of one or more unless otherwise indicated expressly or by context.

Other aspects of the invention are disclosed infra.

DETAILED DESCRIPTION

Topcoat Compositions

In preferred compositions, the first polymer of a topcoat composition can migrate toward the upper surface of the topcoat coating layer during coating of the topcoat composition. In certain systems, this can form a surface layer substantially made up of the first polymer. In preferred aspects, following exposure and post exposure bake (PEB), the topcoat composition layer together with the underlying resist coating layer can be developed, including in a developer comprising an organic solvent. In such systems, the organic developer can remove unexposed regions of both the topcoat and photoresist layer and the surface layer of the exposed regions. When used in immersion lithography, preferred topcoat compositions can exhibit reduced migration (leaching) of photoresist materials into an immersion fluid.

The topcoat compositions can be used together with photoresist compositions at a variety of radiation wavelengths, for example, wavelengths of sub-400 nm, sub-300 or sub-200 nm, or with 248 nm, 193 nm and EUV (e.g., 13.5 nm) exposure wavelengths being preferred. The compositions can further be used in electron beam (E-beam) exposure processes.

In preferred embodiments, the topcoat compositions comprise one or more second or matrix polymers (distinct from the first polymer). Preferred second polymers may comprise acid labile groups. An acid labile group is a chemical moiety that readily undergoes deprotection reaction in the presence of an acid. Such preferred second or matrix polymer as part of a layer of the topcoat composition undergoes a change in solubility in a developer described herein as a result of reaction with acid generated from the photoacid and/or thermal acid generator during lithographic processing, particularly following softbake, exposure to activating radiation and post exposure bake. This results from acid-induced cleavage of the acid labile group, causing a change in polarity of the second polymer. The acid labile group can be chosen, for example, from tertiary alkyl carbonates, tertiary alkyl esters, tertiary alkyl ethers, acetals and ketals. Preferably, the acid labile group suitably is an ester group that contains a tertiary non-cyclic alkyl carbon or a tertiary alicyclic carbon covalently linked to a carboxyl oxygen of an ester of the second matrix polymer. The cleavage of such acid labile groups results in the formation of carboxylic acid groups. Suitable acid labile-group containing units include, for example, acid-labile (alkyl)acrylate units, such as t-butyl (meth)acrylate, 1-methylcyclopentyl (meth)acrylate, 1-ethylcyclopentyl (meth)acrylate, 1-isopropylcyclopentyl (meth)acrylate, 1-propylcyclopentyl (meth)acrylate, 1-methylcyclohexyl (meth)acrylate, 1-ethylcyclohexyl (meth)acrylate, 1-isopropylcyclohexyl (meth)acrylate, 1-propylcyclohexyl (meth)acrylate, t-butyl methyladamantyl(meth)acrylate, ethylfenchyl(meth)acrylate, and the like, and other cyclic, including alicyclic, and non-cyclic (alkyl) acrylates. Acetal and ketal acid labile groups also can be substituted for the hydrogen atom at the terminal of an alkali-soluble group such as a carboxyl group or hydroxyl group, so as to be bonded with an oxygen atom. When acid is generated, the acid cleaves the bond between the acetal or ketal group and the oxygen atom to which the acetal-type acid-dissociable, dissolution-inhibiting group is bonded. Exemplary such acid labile groups are described, for example, in U.S. Pat. Nos. 6,057,083, 6,136,501 and 8,206,886 and European Pat. Pub. Nos. EP01008913A1 and EP00930542A1. Also suitable are acetal and ketal groups as part of sugar derivative structures, the cleavage of which would result in the formation of hydroxyl groups, for example, those described in U.S. Patent Application No. US2012/0064456A1.

For use with photoresists imaged at wavelengths of 200 nm or greater such as 248 nm, suitable resin materials of the present topcoat compositions (including resin materials for use as second polymers of the present topcoat compositions) include, for example, phenolic resins that contain acid-labile groups. Particularly preferred resins of this class include: (i) polymers that contain polymerized units of a vinyl phenol and an acid labile (alkyl) acrylate as described above, such as polymers described in U.S. Pat. Nos. 6,042,997 and 5,492,793; (ii) polymers that contain polymerized units of a vinyl phenol, an optionally substituted vinyl phenyl (e.g., styrene) that does not contain a hydroxy or carboxy ring substituent, and an acid labile (alkyl) acrylate such as described above, such as polymers described in U.S. Pat. No. 6,042,997; (iii) polymers that contain repeat units that comprise an acetal or ketal moiety that will react with photoacid, and optionally aromatic repeat units such as phenyl or phenolic groups; such polymers described in U.S. Pat. Nos. 5,929,176 and 6,090,526, and blends of (i) and/or (ii) and/or (iii).

For use with photoresists imaged at certain sub-200 nm wavelengths such as 193 nm, the second or matrix polymer of the present topcoat compositions is typically substantially free (e.g., less than 15 mole %), preferably completely free, of phenyl, benzyl or other aromatic groups where such groups are highly absorbing of the radiation. Suitable polymers that are substantially or completely free of aromatic groups are disclosed in European Patent Publication No. EP930542A1 and U.S. Pat. Nos. 6,692,888 and 6,680,159.

Other suitable second or matrix polymers of the present topcoat compositions include, for example, those which contain polymerized units of a non-aromatic cyclic olefin (endocyclic double bond) such as an optionally substituted norbornene, for example, polymers described in U.S. Pat. Nos. 5,843,624 and 6,048,664. Still other suitable second polymers include polymers that contain polymerized anhydride units, particularly polymerized maleic anhydride and/or itaconic anhydride units, such as disclosed in European Published Application EP01008913A1 and U.S. Pat. No. 6,048,662.

Also suitable as the second or matrix polymer is a resin that contains repeat units that contain a hetero atom, particularly oxygen and/or sulfur (but other than an anhydride, i.e., the unit does not contain a keto ring atom). The heteroalicyclic unit can be fused to the polymer backbone, and can comprise a fused carbon alicyclic unit such as provided by polymerization of a norbornene group and/or an anhydride unit such as provided by polymerization of a maleic anhydride or itaconic anhydride. Such polymers are disclosed in International Pub. No. WO0186353A1 and U.S. Pat. No. 6,306,554. Other suitable hetero-atom group containing matrix polymers include polymers that contain polymerized carbocyclic aryl units substituted with one or more hetero-atom (e.g., oxygen or sulfur) containing groups, for example, hydroxy naphthyl groups, such as disclosed in U.S. Pat. No. 7,244,542.

In the case of sub-200 nm wavelengths such as 193 nm and EUV (e.g., 13.5 nm), the second or matrix polymer of a topcoat composition may include a unit containing a lactone moiety. Suitable monomers for use in the second or matrix polymer containing a lactone moiety include, for example, the following:

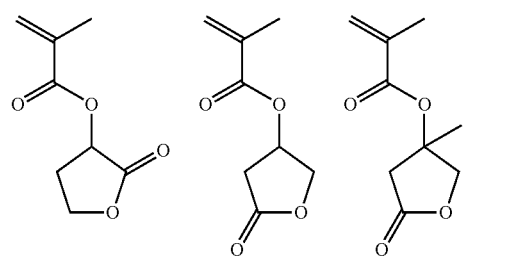

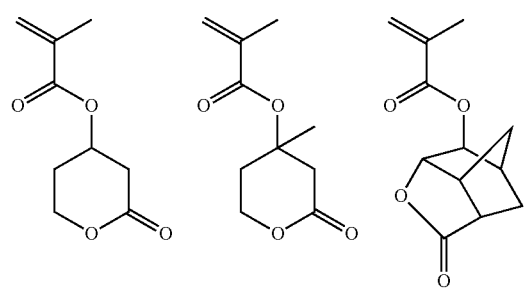

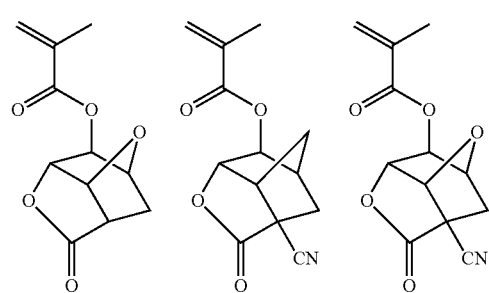

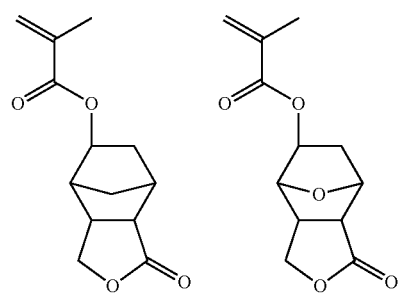

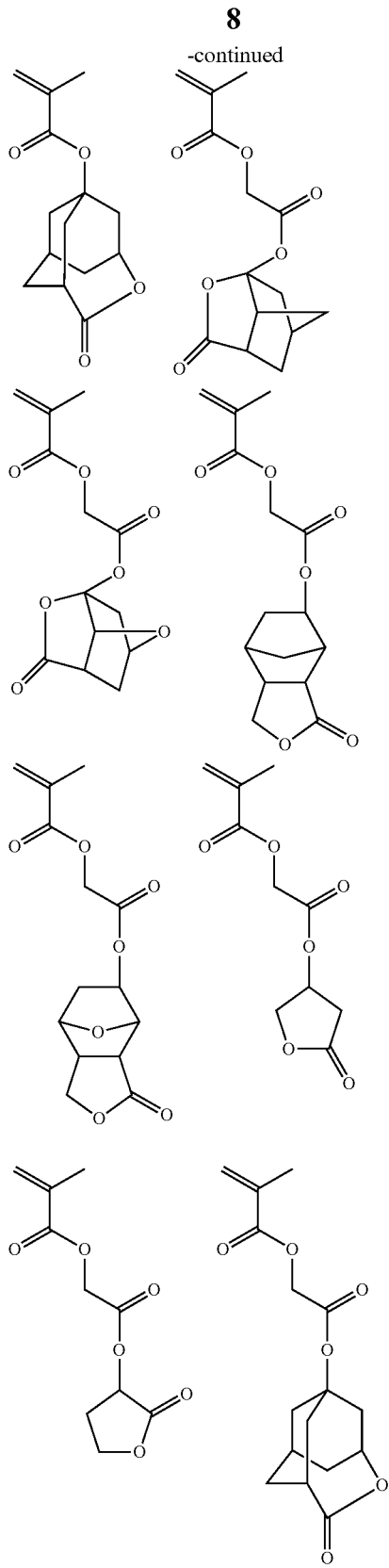

Such a second or matrix polymer further typically includes a unit containing a polar group, which enhances etch resistance of the matrix polymer and photoresist composition and provides additional means to control the dissolution rate of the matrix polymer and photoresist composition. Monomers for forming such a unit include, for example, the following:

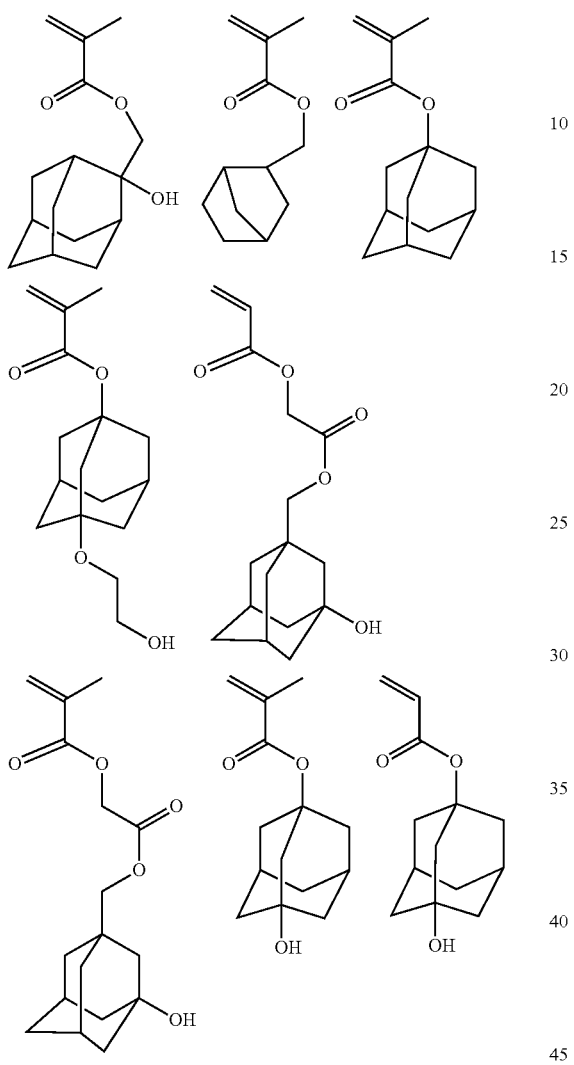

The second or matrix polymer can include one or more additional units of the types described above. Typically, the additional units for the second or matrix polymer will include the same or similar polymerizable group as those used for the monomers used to form the other units of the polymer, but may include other, different polymerizable groups in the same polymer backbone.

In preferred aspects, the second or matrix polymer has a higher surface energy than that of the first or additive polymer, described below, and should be substantially non-miscible with the first polymer. As a result of the difference in surface energies, segregation of the second polymer from the first polymer can take place during spin-coating. A suitable surface energy of the second or matrix polymer is typically from 20 to 50 mN/m, preferably from 30 to 40 mN/m.

While not to be limited thereto, exemplary second or matrix polymers of preferred topcoat compositions include, for example, the following:

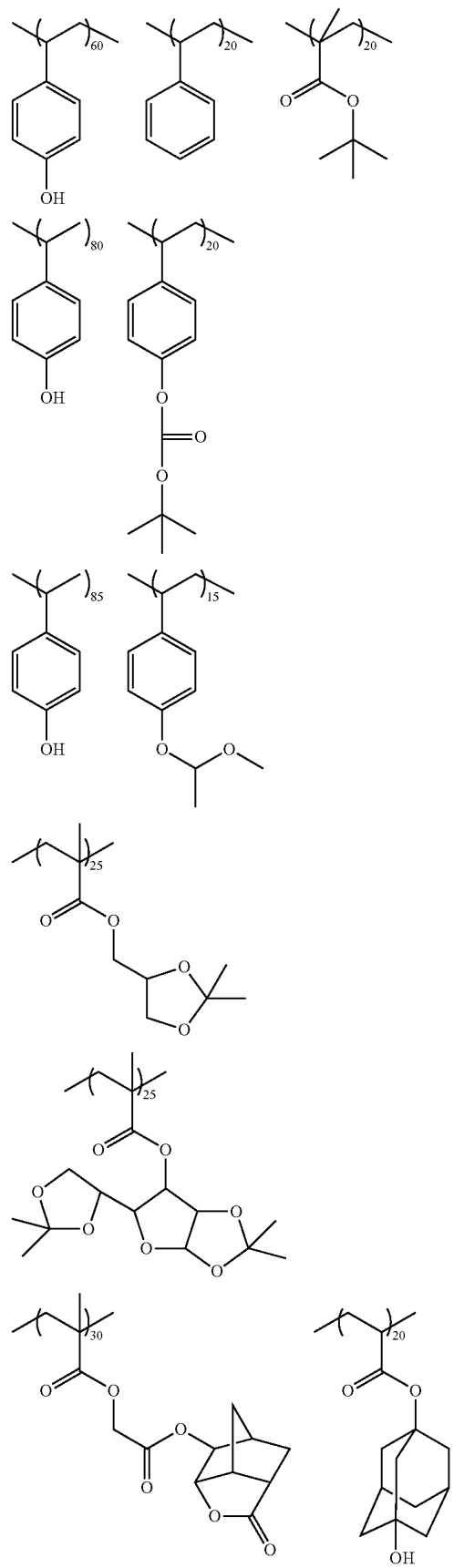

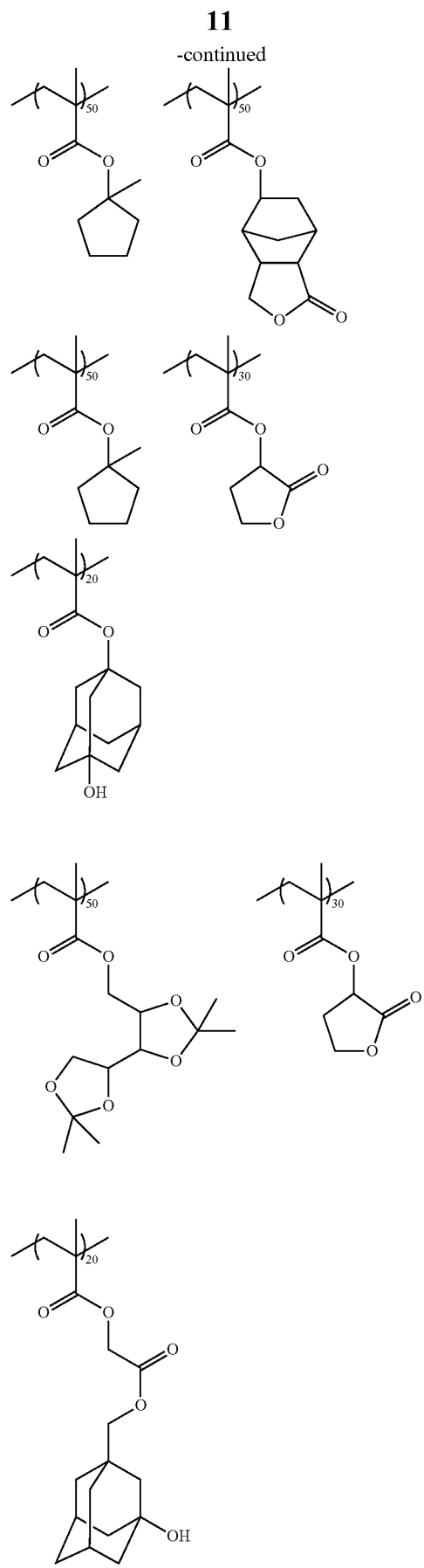
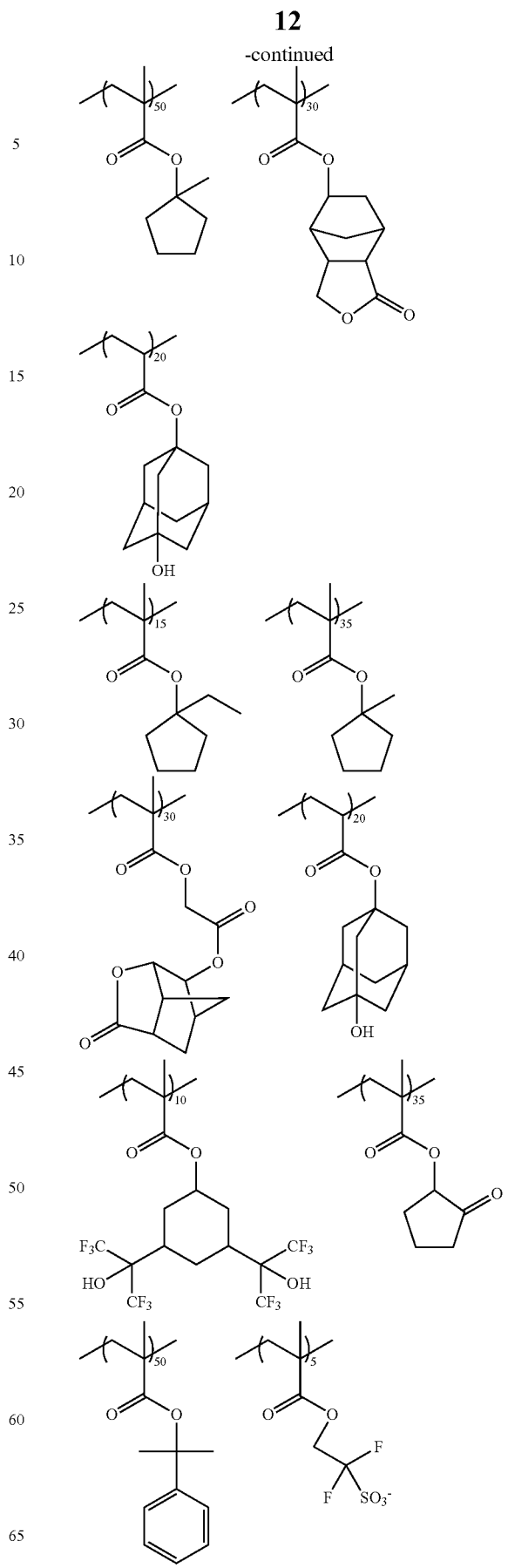

Suitable second or matrix polymers for use in topcoat compositions of the invention are commercially available and can readily be made by persons skilled in the art. The second polymer is present in preferred topcoat compositions in an amount sufficient to render an exposed coating layer of the resist developable in a suitable developer solution. Typically, the second polymer is present in the composition in an amount of from 50 to 95 wt % based on total solids of the topcoat composition. The weight average molecular weight $M_w$ of the second polymer is typically less than 100,000, for example, from 3000 to 100,000, more typically from 3000 to 15,000. Blends of two or more of the above-described second polymers can suitably be used in the topcoat compositions of the invention.

The first or additive polymer of a topcoat composition is preferably a material that has a lower surface energy than that of the second polymer and should be substantially non-miscible with the second polymer. In this way, segregation or migration of the first polymer to the top or upper portions of an applied topcoat layer during the coating process is facilitated. While the desired surface energy of the first polymer will depend on the particular second polymer and its surface energy, the first polymer surface energy is typically from 18 to 40 mN/m, preferably from 20 to 35 mN/m and more preferably from 29 to 33 mN/m. While the first polymer migrates to the upper surface of the topcoat layer during the coating process, it is preferable that there be some intermixing between the first polymer and second or matrix polymer immediately beneath the resist surface. The extent of intermixing will depend, for example, on the difference in surface energy (SE) between the second or matrix polymer (MP) and first or additive polymer (AP) ($\Delta SE = SE_{MP} - SE_{AP}$). For given first or matrix and second or additive polymers, the degree of intermixing can be increased with reduced $\Delta SE$. The $\Delta SE$ is typically from 2 to 32 mN/m, preferably from 5 to 15 mN/m.

As discussed, the first or additive polymers useful in the topcoat compositions are copolymers that have a plurality of distinct repeat units, for example, two, three or four distinct repeat units.

The first polymer is preferably free of silicon. Silicon-containing polymers exhibit a significantly lower etch rate than organic polymers in certain etchants. As a result, aggregation of a silicon-containing first polymer at the surface of an organic second polymer-based topcoat layer can cause cone defects during the etching process. The first polymer may contain fluorine or can be free of fluorine. Preferred first polymers are soluble in the same organic solvent(s) used to formulate the topcoat composition. Preferred first polymers also will be soluble or become soluble upon post exposure bake (e.g., 120° C. for 60 seconds) in organic developers used in negative tone development processes.

As discussed, the first polymer preferably may contain a first unit formed from one or more monomer corresponding to the following Formula (I):

$$X_1-R_1-X_2-R_2-X_3 \qquad (I)$$

wherein $X_1$ is a polymerizable functional group such as an acrylate or alkylacrylate such as a methacrylate; $R_1$ may be an optionally substituted linear, branched or cyclic aliphatic group (including alkyl) having 1 to 30 carbon atoms or an optionally substituted aromatic group such as optionally substituted phenyl or naphthyl, and preferably $R_1$ is $C_{1-15}$ alkyl and optionally fluorinated; $X_2$ is a basic moiety such as a nitrogen and may be a component of or taken together with $R_1$ (e.g. $R_1$ and $X_2$ may combine to form a piperdinyl moiety); $R_2$ is an acid labile group; and $X_3$ may be an optionally substituted linear, branched or cyclic aliphatic group (including alkyl) having 1 to 30 carbon atoms or an optionally substituted aromatic group such as optionally substituted phenyl or naphthyl.

The polymerizable functional group $X_1$ can be chosen, for example, from the following general formulae (P-1), (P-2) and (P-3):

(P-1)

wherein $R_2$ is chosen from hydrogen, fluorine and fluorinated and non-fluorinated C1 to C3 alkyl; and X is oxygen or sulfur;

(P-2)

wherein $R_3$ is chosen from hydrogen, fluorine and fluorinated and non-fluorinated C1 to C3 alkyl; and

(P-3)

wherein m is an integer from 0 to 3.

Exemplary suitable monomers of Formula (I) include the following.

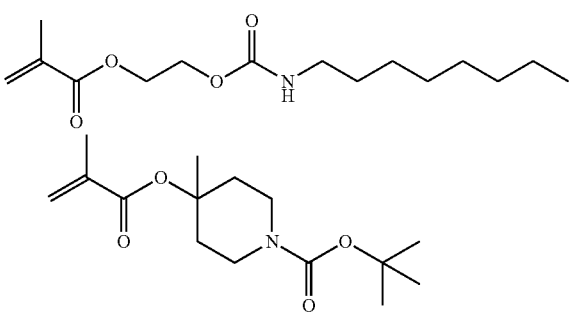

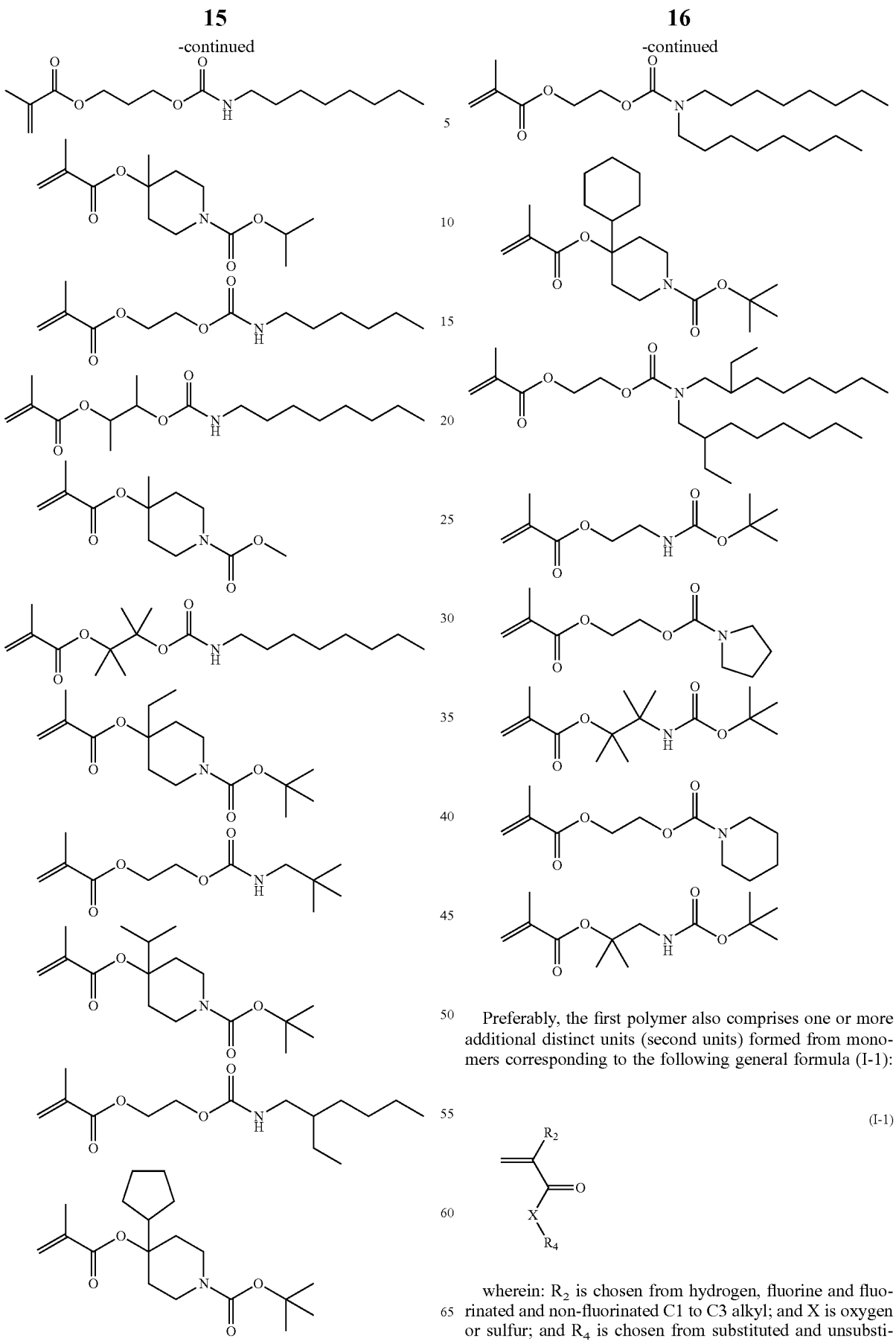

Preferably, the first polymer also comprises one or more additional distinct units (second units) formed from monomers corresponding to the following general formula (I-1):

(I-1)

wherein: $R_2$ is chosen from hydrogen, fluorine and fluorinated and non-fluorinated C1 to C3 alkyl; and X is oxygen or sulfur; and $R_4$ is chosen from substituted and unsubstituted C1 to C20 linear, branched and cyclic hydrocarbons, preferably fluorinated and non-fluorinated C1 to C15 alkyl, more preferably fluorinated and non-fluorinated C3 to C8 alkyl and most preferably fluorinated and non-fluorinated C4 to C5 alkyl, with $R_4$ preferably being branched to provide a higher water receding contact angle when used in immersion lithography, and $R_4$ substitutions of haloalkyl and haloalcohol such as fluoroalkyl and fluoroalcohol being suitable.

As discussed, various moieties of monomers, polymers and other materials may be optionally substituted (or stated to be "substituted or unsubstituted"). A "substituted" substituent may be substituted at one or more available positions, typically 1, 2, or 3 positions by one or more suitable groups such as e.g. halogen (particularly F, Cl or Br); cyano; nitro; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl, haloalkyl particularly $C_{1-8}$ haloalkyl such as $CF_3$; —CONHR, —CONRR' where R and R' are optionally substituted $C_{1-8}$alkyl; —COOH, COC, >C=O; and the like.

Exemplary suitable monomers of Formula (I-1) are described below, but are not limited to these structures. For purposes of these structures, "$R_2$" and "X" are as defined above for Formula I-1.

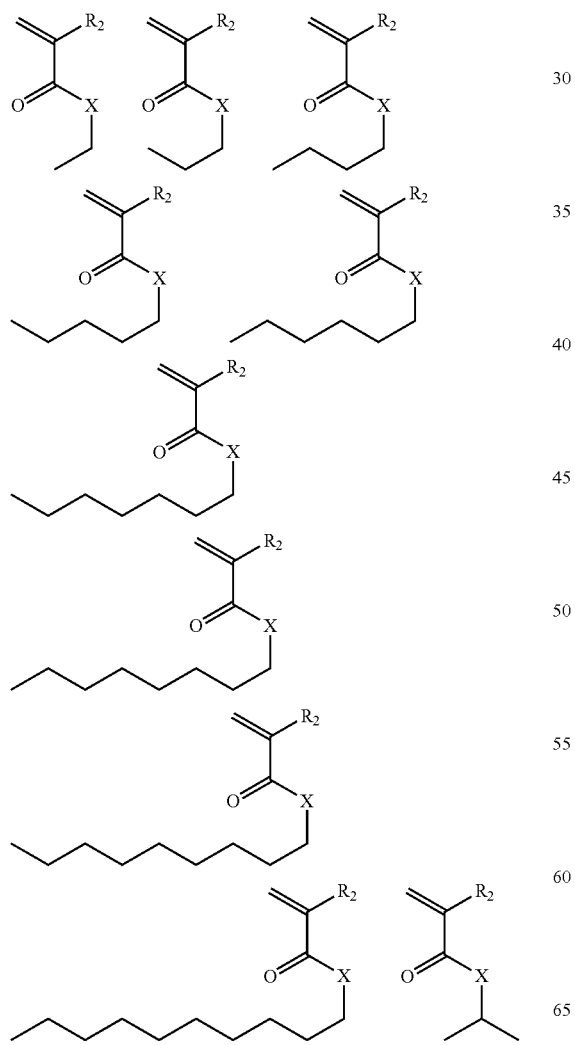
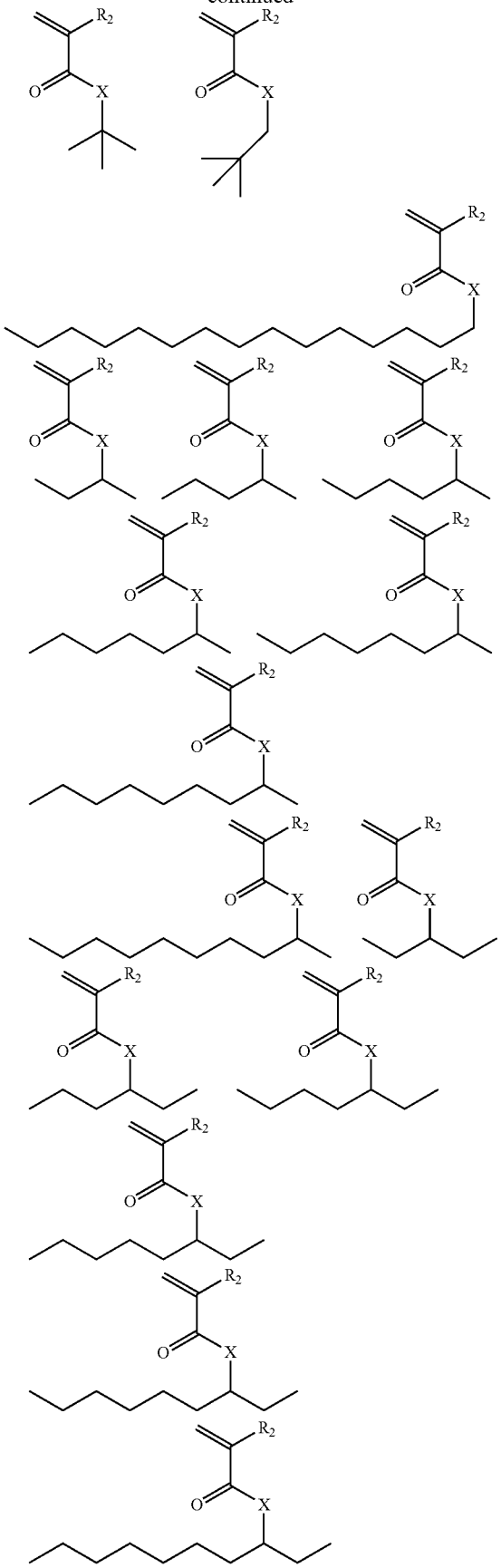

-continued
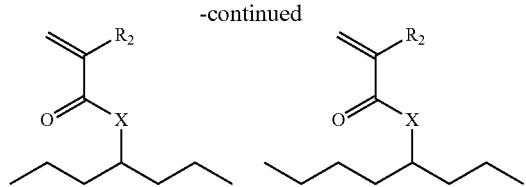
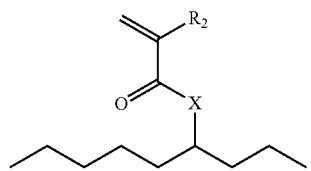
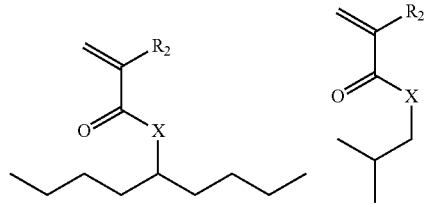
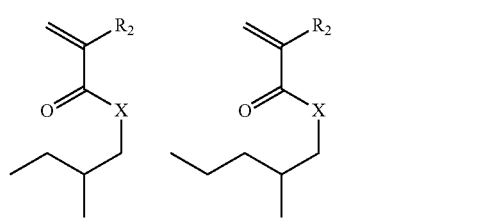
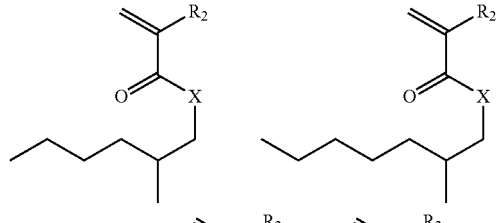
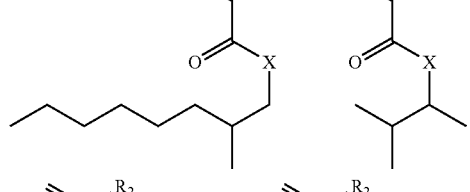
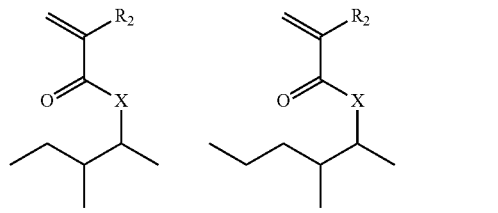
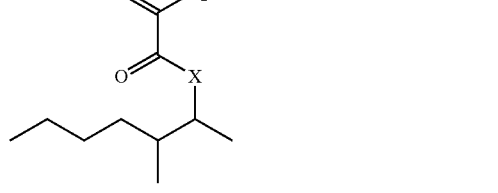
-continued
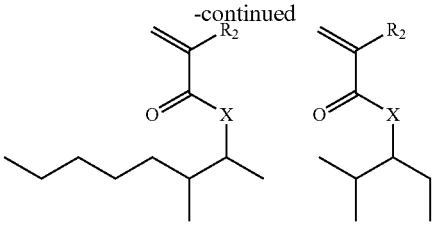
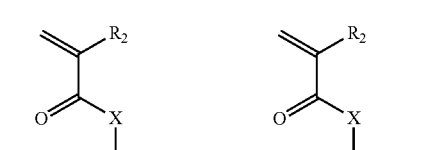
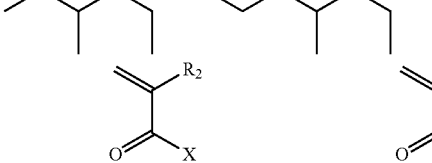
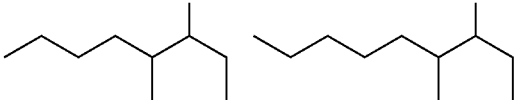
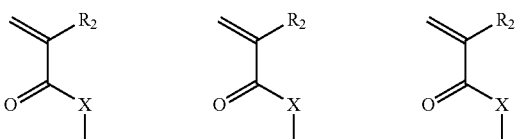
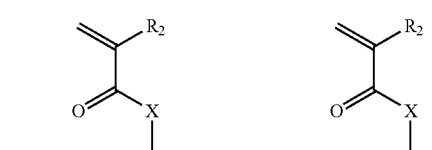
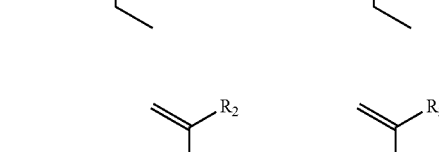
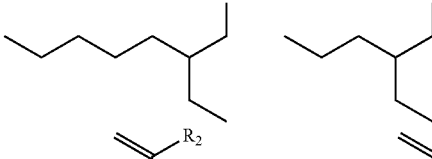
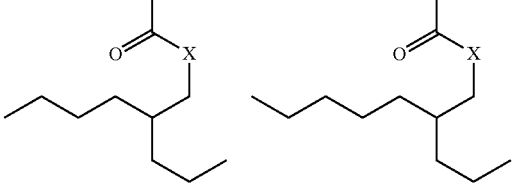

-continued
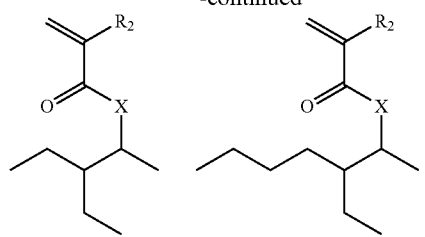
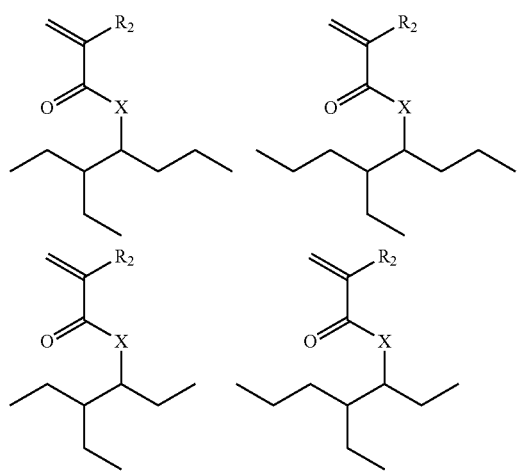
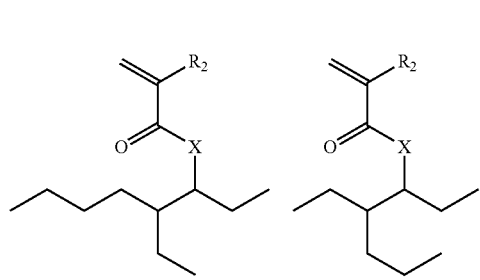
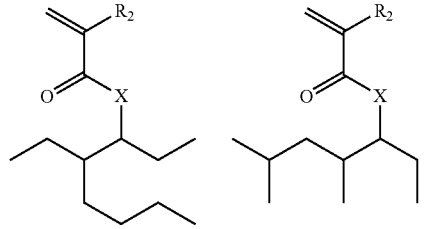
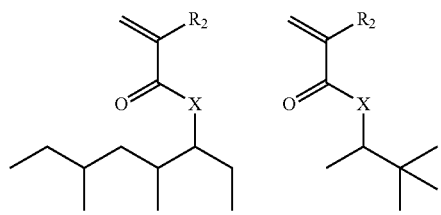
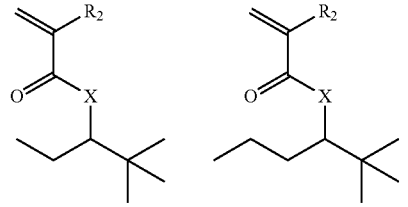
-continued
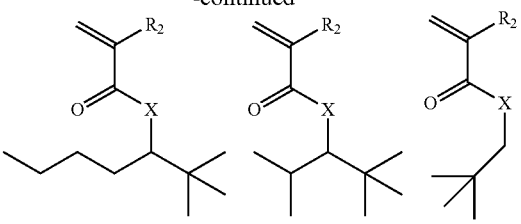
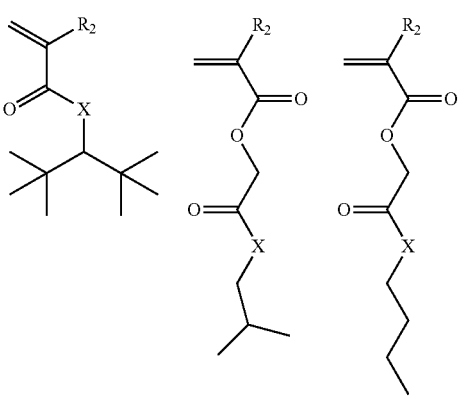
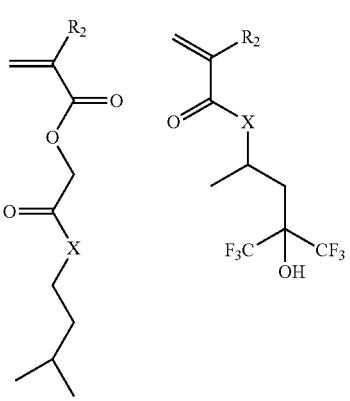
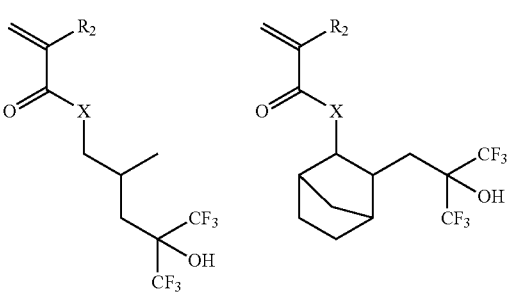
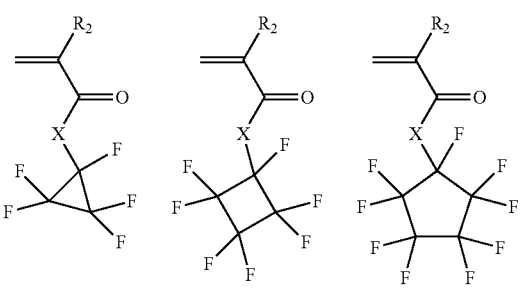

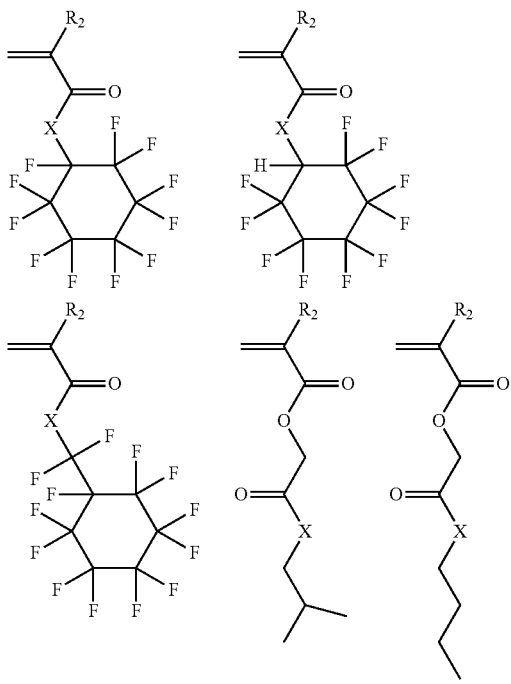
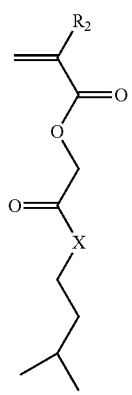
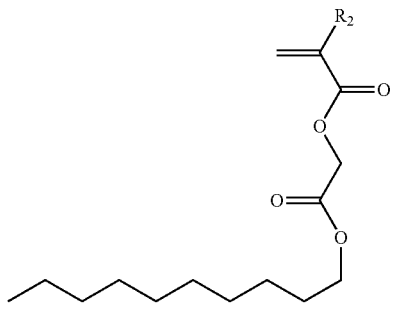
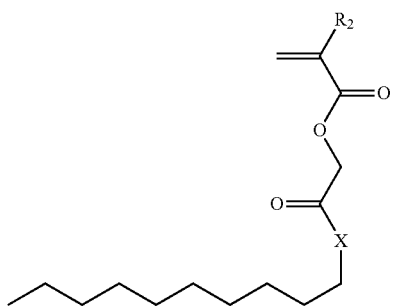
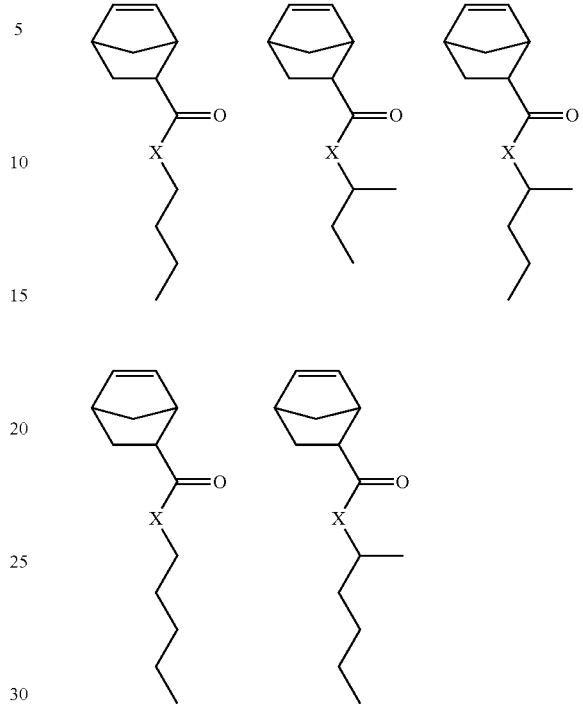

Exemplary first polymers useful in the topcoat compositions include the following. For purposes of these structures, "$R_2$" and "X" are defined as follows: each $R_2$ is independently chosen from hydrogen, fluorine and fluorinated and non-fluorinated C1 to C3 alkyl; and each X is independently oxygen or sulfur. Exemplary first polymers useful in the present photoresist compositions include the following. For purposes of these structures, "$R_2$" and "X" are defined as follows: each $R_2$ is independently chosen from hydrogen, fluorine and fluorinated and non-fluorinated C1 to C3 alkyl; and each X is independently oxygen or sulfur.

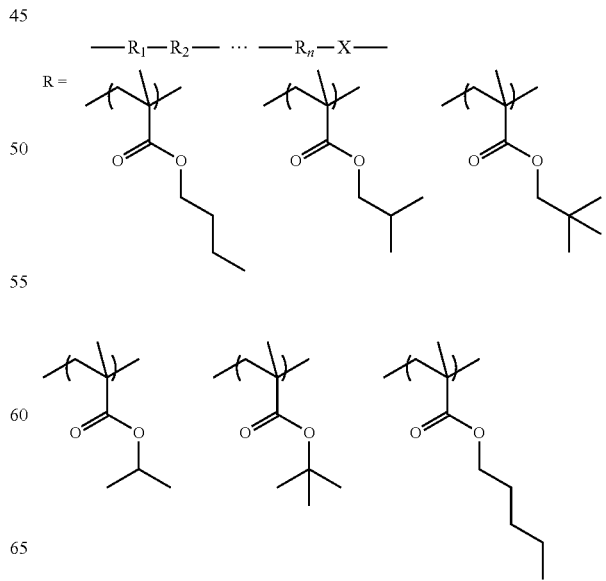

-continued
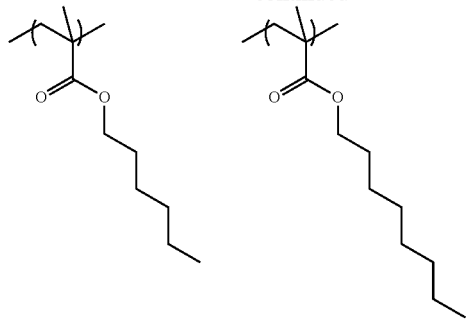
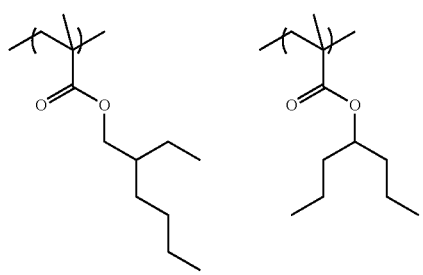
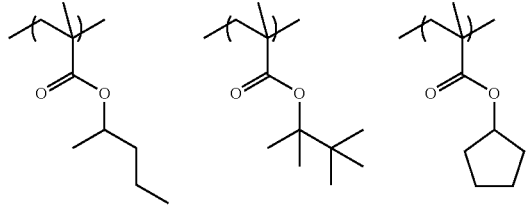
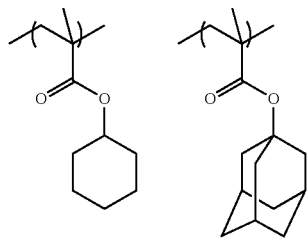
X =
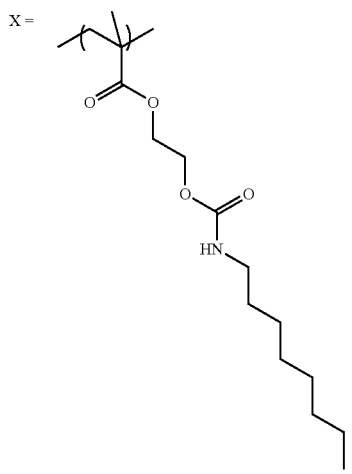
-continued
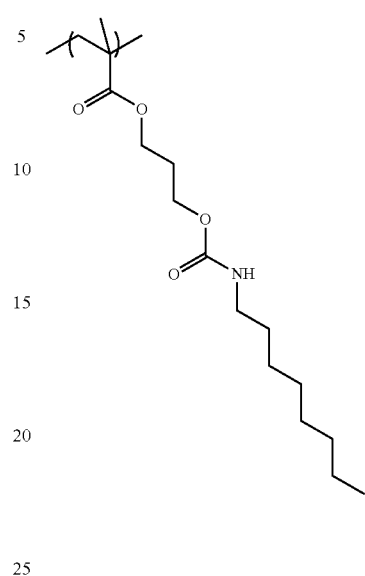
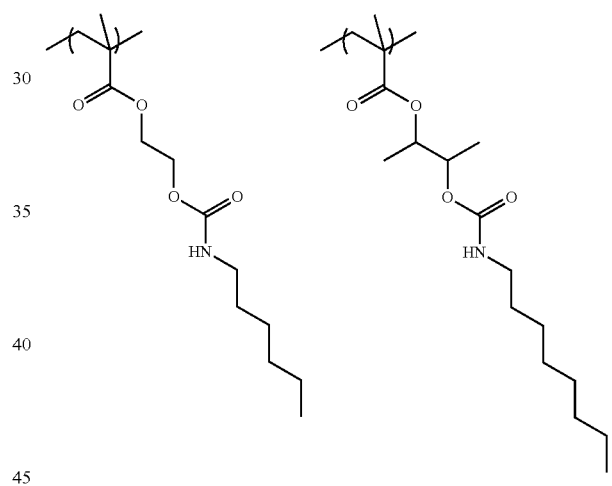
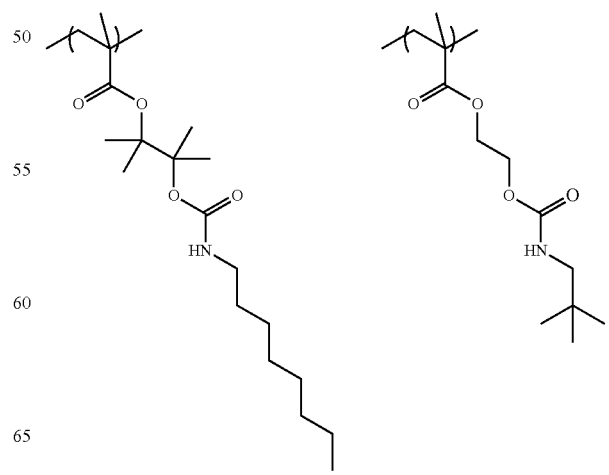

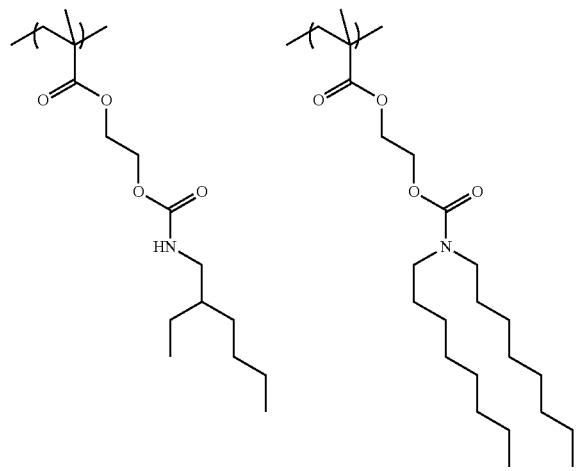
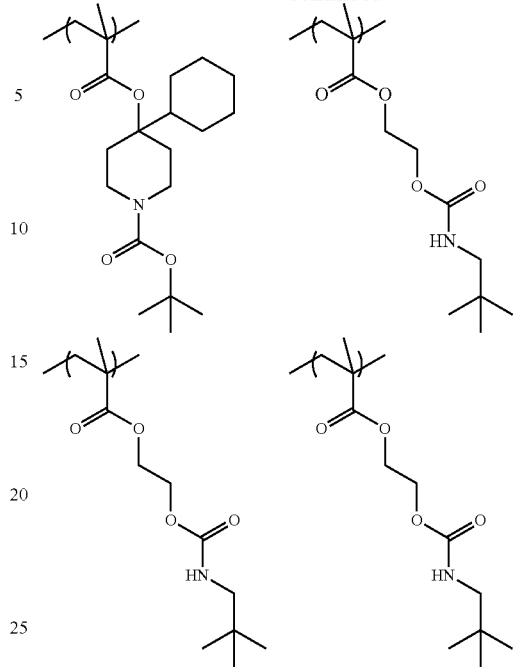
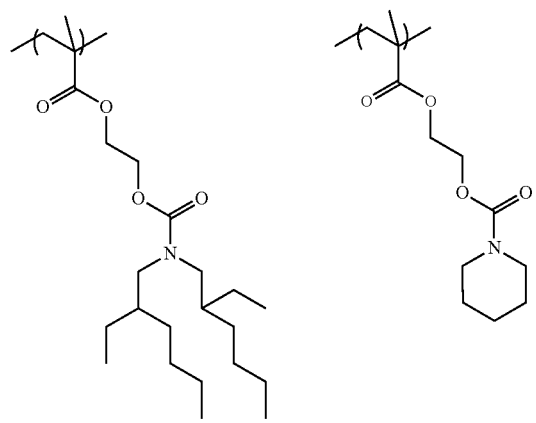
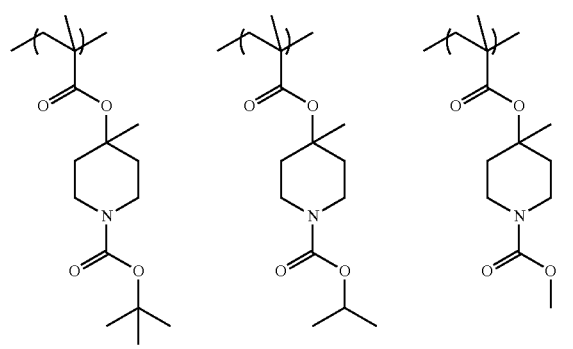
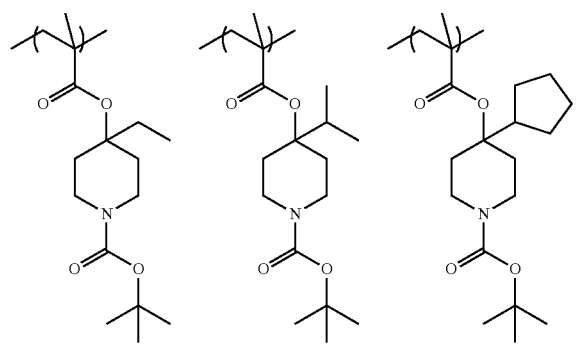

The first polymer is typically present in the topcoat composition in a relatively small amount, for example, in an amount of from 0.1 to 10 wt %, preferably from 0.5 to 5 wt %, more preferably from 1 to 3 wt %, based on total solids of the photoresist composition. The content of the first or additive polymer will depend, for example, on the content (if any) of acid generator in the topcoat layer, the content of the nitrogen-containing groups in the first polymer, and whether the lithography is a dry or immersion-type process. For example, the first polymer lower limit for immersion lithography is generally dictated by the need to prevent leaching of the resist components. An excessively high first polymer content may result in pattern degradation. The weight average molecular weight of the additive polymer is typically less than 400,000, preferably from 3000 to 50,000, more preferably from 3000 to 25,000. Suitable first polymers and monomers for making the first polymers for use in the topcoat compositions of the invention are commercially available and/or can be made by persons skilled in the art.

As discussed above, in certain embodiments, the topcoat compositions may contain one or more acid generator compounds, for example, one or more thermal acid generator compounds and/or one or more photoacid generator compounds. Optionally, the topcoat compositions may be free of such acid generator compounds. In this regard, acid generator compounds can be provided by migration from the underlying photoresist into the topcoat layer during processing making their separate addition as part of the topcoat compositions unnecessary. Suitable thermal acid generators include ionic or substantially neutral thermal acid generators, for example, an ammonium arenesulfonate salt. Suitable PAGs are known in the art of chemically amplified photoresists and include, for example: onium salts, for example, triphenyl sulfonium salts, nitrobenzyl derivatives, sulfonic acid esters, diazomethane derivatives, glyoxime derivatives, sulfonic acid ester derivatives of an N-hydroxy-imide compound and halogen-containing triazine compounds. If employed, the one or more acid generators may be utilized in relatively small amounts in a topcoat composition, for example, 0.1 to 8 wt % of the total of the dry components of the composition (all components except solvent carrier), such as about 2 wt % of the total dry components. Such use of one or more acid generator compounds can favorably impact lithographic performance, particularly resolution, of the developed image patterned in an underlying resist layer.

In certain embodiments, a topcoat composition may further comprise an additional acid quencher compounds. Suitable quencher compounds may be non-polymeric and have molecular weights such as below about 1,500, 1,000, or 500. Suitable quencher compounds include for example substituted aliphatic and aromatic amines as well as carbamate compounds, including carbamate compounds that will react with acid during lithographic processing of a coating layer of a topcoat composition as disclosed herein. A particularly preferred quencher compound is the following:

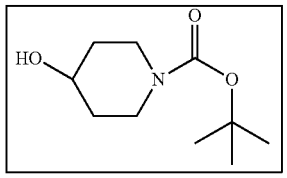

Such quencher compounds may be suitably present in a topcoat compound in a wide range of amounts, including for example, from 1, 2, 3, 4 or 5 to 10, 20, 30, 40 or 50 weight percent or more relative to the weight of the first polymer present in the topcoat composition.

Preferred topcoat composition layers will have an index of refraction of about 1.4 or greater at 193 nm including about 1.47 or greater at 193 nm. Additionally, for any particular system, the index of refraction can be tuned by changing the composition of one or more polymers of the topcoat composition, including by altering the ratio of components of a polymer blend, or composition of any of the polymer(s) of a topcoat composition. For instance, increasing the amount of organic content in a topcoat layer composition can provided increased refractive index of the layer.

Preferred topcoat layer compositions will have a refractive index between of the immersion fluid and the refractive index of the photoresist at the target exposure wavelength, for example, 193 nm or 248 nm.

Typical solvent materials to formulate and cast a topcoat composition are any which dissolve or disperse the components of the topcoat layer composition but do not appreciably dissolve an underlying photoresist layer. More particularly, suitable solvents to formulate a topcoat composition include one or more of, but are not limited to, alcohols such as n-butanol, alkylene glycols, such as propylene glycol. Alternatively non-polar solvents such as aliphatic and aromatic hydrocarbons, and alkyl ethers such as dodecane, isooctane and isopentyl ether may be used. One or more solvent in the solvent system can individually be in a substantially pure form, meaning isomers of the solvent molecule are present in that solvent in an amount less than 5 wt %, for example, less than 2 wt % or less than 1 wt %. Optionally, the solvent can include a mixture of isomers of the solvent molecule, wherein the isomers are present in an amount greater than 5 wt %, for example, greater than 10 wt %, greater than 20 wt %, greater than 40 wt %, greater than 60 wt %, greater than 80 wt % or greater than 90 wt %. Preferably, a mixture of different solvents, for example, two, three or more solvents, is used to achieve effective phase separation of the segregating, first additive polymer from other polymer(s) in the composition and to reduce the viscosity of the formulation which allows for reduction in the dispense volume.

In an exemplary aspect, a three-solvent system can be used in the topcoat compositions of the invention. The solvent system can include, for example, a primary solvent, a thinner solvent and an additive solvent. The primary solvent typically exhibits excellent solubility characteristics with respect to the non-solvent components of the topcoat composition. While the desired boiling point of the primary solvent will depend on the other components of the solvent system, the boiling point is typically less than that of the additive solvent, with a boiling point of from 120 to 140° C. such as about 130° C. being typical. Suitable primary solvents include, for example, C4 to C8 n-alcohols, such as n-butanol, isobutanol, 2-methyl-1-butanol, isopentanol, 2,3-dimethyl-1-butanol, 4-methyl-2-pentanol, isohexanol and isoheptanol, isomers thereof and mixtures thereof. The primary solvent is typically present in an amount of from 30 to 80 wt % based on the solvent system.

The thinner solvent is present to lower the viscocity and improve coating coverage at a lower dispensing volume. The thinner solvent is typically a poorer solvent for the non-solvent components of the composition relative to the primary solvent. While the desired boiling point of the thinner solvent will depend on the other components of the solvent system, a boiling point of from 140 to 180° C. such as about 170° C. is typical. Suitable thinner solvents include, for example, alkanes such as C8 to C12 n-alkanes, for example, n-octane, n-decane and dodecane, isomers thereof and mixtures of isomers thereof; and/or alkyl ethers such as those of the formula $R_1$—O—$R_2$, wherein $R_1$ and $R_2$ are independently chosen from $C_2$ to $C_8$ alkyl, $C_2$ to $C_6$ alkyl and $C_2$ to $C_4$ alkyl. The alkyl ether groups can be linear or branched, and symmetric or asymmetric. Particularly suitable alkyl ethers include, for example, isobutyl ether, isopentyl and isobutyl isohexyl, isomers thereof and mixtures thereof. The thinner solvent is typically present in an amount of from 10 to 70 wt % based on the solvent system.

The additive solvent is present to facilitate phase separation between the phase segregation polymer and other polymer(s) in the topcoat composition to facilitate a self-segregating topcoat structure. In addition, the higher boiling point additive solvent can reduce the tip drying effect during coating. It is typical for the additive solvent to have a higher boiling point than the other components of the solvent system. While the desired boiling point of the additive solvent will depend on the other components of the solvent system, a boiling point of from 170 to 200° C. such as about 190° C. is typical. Suitable additive solvents include, for example, hydroxy alkyl ethers, such as those of the formula:

$R_1$—O—$R_2$—O—$R_3$—OH wherein $R_1$ is an optionally substituted C1 to C2 alkyl group and $R_2$ and $R_3$ are independently chosen from optionally substituted C2 to C4 alkyl groups, and mixtures of such hydroxy alkyl ethers including isomeric mixtures. Exemplary hydroxy alkyl ethers include dialkyl glycol mono-alkyl ethers and isomers thereof, for example, diethylene glycol monomethyl ether, dipropylene glycol monomethyl ether, isomers thereof and mixtures thereof. The additive solvent is typically present in an amount of from 3 to 15 wt % based on the solvent system.

A particularly suitable three-solvent system includes 4-methyl-2-pentanol/isopentyl ether/dipropylene glycol monomethyl ether in a ratio by weight of 49/45/6. While the exemplary solvent system has been described with respect to a three-component system, it should be clear that additional solvents may be used. For example, one or more additional primary solvent, thinner solvent, additive solvent and/or other solvent may be employed.

A topcoat composition may be suitably prepared by admixture of the polymers into one or more polar solvents such as those identified above or alternatively one or more non-polar solvents such as the aliphatic and aromatic hydrocarbons identified above. The viscocity of the entire composition is typically from 1.5 to 2 centipoise (cp).

The examples which follow provide exemplary preparations of topcoat compositions of the invention.

Photoresists

A wide variety of photoresist compositions may be used in combination with topcoat compositions and processes of the invention.

Typical photoresists for use in accordance with the invention include positive-acting or negative-acting chemically amplified photoresists, i.e., positive-acting resist compositions which undergo a photoacid-promoted deprotection reaction of acid labile groups of one or more composition components to render exposed regions of a coating layer of the resist more soluble in an aqueous developer than unexposed regions, and negative-acting resist compositions which undergo a photoacid-promoted crosslinking reaction to render exposed regions of a coating layer of the resist less developer soluble than unexposed regions. Of these, positive-acting materials are typical. Ester groups that contain a tertiary non-cyclic alkyl carbon (e.g., t-butyl) or a tertiary alicyclic carbon (e.g., methyladamantyl) covalently linked to the carboxyl oxygen of the ester are often preferred photoacid-labile groups of polymers employed in photoresists of lithography systems of the invention. Acetal photoacid-labile groups also will be preferred.

The photoresists useful in accordance with the invention typically comprise a polymer component and a photoactive component. Typically, the polymer has functional groups that impart alkaline aqueous developability to the resist composition. For example, typical are resin binders that comprise polar functional groups such as hydroxyl or carboxylate. Typically, a polymer component is used in a resist composition in an amount sufficient to render the resist developable with an aqueous alkaline solution.

For imaging at wavelengths greater than 200 nm, such as 248 nm, phenolic resins are typical. Typical phenolic resins are poly (vinylphenols) which may be formed by block polymerization, emulsion polymerization or solution polymerization of the corresponding monomers in the presence of a catalyst. Vinylphenols useful for the production of polyvinyl phenol resins may be prepared, for example, by hydrolysis of commercially available coumarin or substituted coumarin, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or nonsubstituted hydroxybenzaldehydes with malonic acid. Preferred polyvinylphenol resins prepared from such vinylphenols have a molecular weight range of from about 2,000 to about 60,000 daltons.

Other typical resins that have acid-labile deblocking groups for use in a positive-acting chemically-amplified photoresist of the invention have been disclosed in European Published Application EP0829766A2 (resins with acetal and ketal resins) and European Published Application EP0783136A2 (terpolymers and other copolymers including units of 1) styrene; 2) hydroxystyrene; and 3) acid labile groups, particularly alkyl acrylate acid labile groups such as t-butylacrylate or t-butylmethacrylate). In general, resins having a variety of acid labile groups will be suitable, such as acid sensitive esters, carbonates, ethers, imides, etc. The photoacid labile groups will more typically be pendant from a polymer backbone, although resins that have acid labile groups that are integral to the polymer backbone also may be employed.

For imaging at sub-200 nm wavelengths such as 193 nm, a typical photoresist contains one or more polymers that are substantially, essentially or completely free of phenyl or other aromatic groups. For example, for sub-200 nm imaging, typical photoresist polymers contain less than about 5 mole percent (mole %) aromatic groups, more typically less than about 1 or 2 mole % aromatic groups, more typically less than about 0.1, 0.02, 0.04 and 0.08 mole % aromatic groups, and still more typically less than about 0.01 mole % aromatic groups. Particularly useful polymers are completely free of aromatic groups. Aromatic groups can be highly absorbing of sub-200 nm radiation and thus are generally undesirable for polymers used in photoresists imaged with such short wavelength radiation.

Suitable polymers that are substantially or completely free of aromatic groups and may be formulated with a PAG to provide a photoresist for sub-200 nm imaging are disclosed in European Published Application EP930542A1 and U.S. Pat. Nos. 6,692,888 and 6,680,159.

Suitable polymers that are substantially or completely free of aromatic groups suitably contain acrylate units such as photoacid-labile acrylate units as may be provided by polymerization of methyladamanatylacrylate, methyladamantylmethacrylate, ethylfenchylacrylate, ethylfenchylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride and/or itaconic anhydride; and the like.

Negative-acting photoresist compositions useful in the invention comprise a mixture of materials that will cure, crosslink or harden upon exposure to acid, and a photoactive component of the invention. Particularly useful negative acting compositions comprise a resin binder such as a phenolic resin, a crosslinker component and a photoactive component. Such compositions and the use thereof have been disclosed in European Patent Nos. 0164248B1 and 0232972B1, and in U.S. Pat. No. 5,128,232. Typical phenolic resins for use as the resin binder component include novolaks and poly(vinylphenol)s such as those discussed above. Typical crosslinkers include amine-based materials, including melamine, glycolurils, benzoguanamine-based materials and urea-based materials. Melamine-formaldehyde resins are generally most typical. Such crosslinkers are commercially available, for example: the melamine resins sold by Cytec Industries under the trade names Cymel 300, 301 and 303; glycoluril resins sold by Cytec Industries under the trade names Cymel 1170, 1171, 1172; urea-based resins sold by Teknor Apex Company under the trade names Beetle 60, 65 and 80; and benzoguanamine resins sold by Cytec Industries under the trade names Cymel 1123 and 1125.

For imaging at sub-200 nm wavelengths such as 193 nm, typical negative-acting photoresists are disclosed in International Application Pub. No. WO 03077029.

The resin component of resists useful in the invention is typically used in an amount sufficient to render an exposed coating layer of the resist developable such as with an aqueous alkaline solution. More particularly, a resin binder will suitably comprise 50 to about 90 wt % of total solids of the resist. The photoactive component should be present in an amount sufficient to enable generation of a latent image in a coating layer of the resist. More specifically, the photoactive component will suitably be present in an amount of from about 1 to 40 wt % of total solids of a resist. Typically, lesser amounts of the photoactive component will be suitable for chemically amplified resists.

The resist compositions useful in the invention also comprise a PAG employed in an amount sufficient to generate a latent image in a coating layer of the resist upon exposure to activating radiation. Suitable PAGs are described above with reference to the topcoat compositions.

A typical optional additive of the resists is an added base, particularly tetrabutylammonium hydroxide (TBAH), or tetrabutylammonium lactate, which can enhance resolution of a developed resist relief image. For resists imaged at 193 nm, a typical added base is a hindered amine such as diazabicyclo undecene or diazabicyclononene. The added base is suitably used in relatively small amounts, for example, about 0.03 to 5 wt % relative to the total solids.

Photoresists used in accordance with the invention also may contain other optional materials. For example, other optional additives include anti-striation agents, plasticizers and speed enhancers. Such optional additives typically will be present in minor concentrations in a photoresist composition except for fillers and dyes which may be present in relatively large concentrations, for example, in amounts of from about 5 to 30 wt % based on the total weight of a resist's dry components.

The photoresists useful in the invention are generally prepared following known procedures. For example, a resist of the invention can be prepared as a coating composition by dissolving the components of the photoresist in a suitable solvent, for example, a glycol ether such as 2-methoxyethyl ether (diglyme), ethylene glycol monomethyl ether, propylene glycol monomethyl ether; propylene glycol monomethyl ether acetate; lactates such as ethyl lactate or methyl lactate, with ethyl lactate being preferred; propionates, particularly methyl propionate, ethyl propionate and ethyl ethoxy propionate; a Cellosolve ester such as methyl Cellosolve acetate; an aromatic hydrocarbon such toluene or xylene; or a ketone such as methylethyl ketone, cyclohexanone and 2-heptanone. Typically the solids content of the photoresist varies between 5 and 35 wt % based on the total weight of the photoresist composition. Blends of such solvents also are suitable.

Lithographic Processing

Liquid photoresist compositions can be applied to a substrate such as by spin coating, dipping, roller coating or other conventional coating technique, with spin coating being typical. When spin coating, the solids content of the coating solution can be adjusted to provide a desired film thickness based upon the specific spinning equipment utilized, the viscosity of the solution, the speed of the spinner and the amount of time allowed for spinning.

Photoresist compositions used in accordance with the invention are suitably applied to substrates conventionally used in processes involving coating with photoresists. For example, the composition may be applied over silicon wafers or silicon wafers coated with silicon dioxide for the production of microprocessors and other integrated circuit components. Aluminum-aluminum oxide, gallium arsenide, ceramic, quartz, copper, glass substrates and the like may also be suitably employed. Photoresists also may be suitably applied over an antireflective layer, particularly an organic antireflective layer.

A topcoat composition of the invention can be applied over the photoresist composition by any suitable method such as described above with reference to the photoresist compositions, with spin coating being typical.

Following coating of the photoresist onto a surface, it may be dried by heating to remove the solvent until typically the photoresist coating is tack free, or as discussed above, the photoresist layer may be dried after the topcoat layer composition has been applied and the solvent from both the photoresist composition and topcoat composition layers substantially removed in a single thermal treatment step.

The photoresist layer with topcoat composition layer is then exposed to patterned radiation activating for the photoactive component of the photoresist.

In an immersion lithography system, the space between the exposure tool (particularly the projection lens) and the photoresist coated substrate is occupied by an immersion fluid, such as water or water mixed with one or more additives such as cesium sulfate which can provide a fluid of enhanced refractive index. Typically, the immersion fluid (e.g., water) has been treated to avoid bubbles, for example, degassing the water to avoid nanobubbles.

References herein to "immersion exposing" or other similar term indicates that exposure is conducted with such a fluid layer (e.g. water or water with additives) interposed between an exposure tool and the coated photoresist composition layer. During the exposure step (whether immersion where fluid is interposed, or non-immersion where such fluid is not interposed), the photoresist composition layer is exposed to patterned activating radiation with the exposure energy typically ranging from about 1 to 100 $mJ/cm^2$, dependent upon the exposure tool and the components of the photoresist composition. References herein to exposing a photoresist composition to radiation that is activating for the photoresist indicates that the radiation is capable of forming a latent image in the photoresist such as by causing a reaction of the photoactive component, for example, producing photoacid from a photoacid generator compound.

As discussed above, photoresist compositions may be photoactivated by a short exposure wavelength, particularly a sub-300 and sub-200 nm exposure wavelength, with 248 nm and 193 nm being particularly preferred exposure wavelengths, as well as EUV and 157 nm Following exposure, the film layer of the composition is typically baked at a temperature ranging from about 70° C. to about 160° C.

Thereafter, the film is developed, typically by treatment with an aqueous base developer chosen from quaternary ammonium hydroxide solutions such as a tetra-alkyl ammonium hydroxide solutions; amine solutions, typically a 0.26 N tetramethylammonium hydroxide such as ethyl amine, n-propyl amine, diethyl amine, di-n-propyl amine, triethyl amine, or methyldiethyl amine; alcohol amines such as diethanol amine or triethanol amine; and cyclic amines such as pyrrole or pyridine. In general, development is in accordance with procedures recognized in the art.

Following development of the photoresist coating over the substrate, the developed substrate may be selectively processed on those areas bared of resist, for example by chemically etching or plating substrate areas bared of resist in accordance with procedures known in the art. For the manufacture of microelectronic substrates, for example, the manufacture of silicon dioxide wafers, suitable etchants include a gas etchant such as a halogen plasma etchant such as a chlorine- or fluorine-based etchant such a $Cl_2$ or The following non-limiting examples are illustrative of the invention.

EXAMPLES

Second Polymer Syntheses

The following monomers were employed in the syntheses of topcoat polymers as described below:

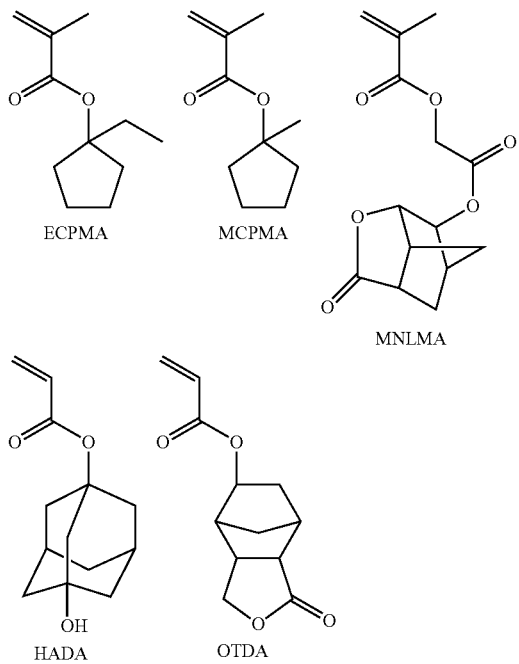

Example 1: Synthesis of Poly(ECPMA/MCPMA/MNLMA/HADA) (MP-1)

Monomers of ECPMA (5.092 g), MCPMA (10.967 g), MNLMA (15.661 g) and HADA (8.280 g) were dissolved in 60 g of propylene glycol monomethyl ether acetate (PGMEA). The monomer solution was degassed by bubbling with nitrogen for 20 min PGMEA (27.335 g) was charged into a 500 mL three-neck flask equipped with a condenser and a mechanical stirrer and was degassed by bubbling with nitrogen for 20 min. Subsequently, the solvent in the reaction flask was brought to a temperature of 80° C. V601 (dimethyl-2,2-azodiisobutyrate) (0.858 g) was dissolved in 8 g of PGMEA and the initiator solution was degassed by bubbling with nitrogen for 20 min. The initiator solution was added into the reaction flask and then monomer solution was fed into the reactor dropwise over a 3 hour period under rigorous stirring and nitrogen environment. After monomer feeding was complete, the polymerization mixture was left standing for one additional hour at 80° C. After a total of 4 hours of polymerization time (3 hours of feeding and 1 hour of post-feeding stirring), the polymerization mixture was allowed to cool down to room temperature. Precipitation was carried out in methyl tert-butyl ether (MTBE) (1634 g). The power precipitated was collected by filtration, air-dried overnight, re-dissolved in 120 g of THF, and re-precipitated into MTBE (1634 g). The final polymer was filtered, air-dried overnight and further dried under vacuum at 60° C. for 48 hours to give 31.0 g of poly(ECPMA/MCPMA/MNLMA/HADA) (15/35/30/20) copolymer (MP-1) (Mw=20,120 and Mw/Mn=1.59).

Example 2: Synthesis of Poly(MCPMA/OTDA/HADA) (MP-2)

Monomers of MCPMA (17.233 g), OTDA (13.695 g) and HADA (9.108 g) were dissolved in 60 g of PGMEA. The monomer solution was degassed by bubbling with nitrogen for 20 min. PGMEA (30.837 g) was charged into a 500 mL three-neck flask equipped with a condenser and a mechanical stirrer and was degassed by bubbling with nitrogen for 20 min. Subsequently the solvent in the reaction flask was brought to a temperature of 80° C. V601 (dimethyl-2,2-azodiisobutyrate) (2.359 g) was dissolved in 8 g of PGMEA and the initiator solution was degassed by bubbling with nitrogen for 20 min. The initiator solution was added into the reaction flask and then monomer solution was fed into the reactor dropwise over the 3 hour period under rigorous stirring and nitrogen environment. After monomer feeding was complete, the polymerization mixture was left standing for one additional hour at 80° C. After a total of 4 hours of polymerization time (3 hours of feeding and 1 hour of post-feeding stirring), the polymerization mixture was allowed to cool down to room temperature. Precipitation was carried out MTBE (1694 g). The power precipitated was collected by filtration, air-dried overnight, re-dissolved in 120 g of THF, and re-precipitated into MTBE (1694 g). The final polymer was filtered, air-dried overnight and further dried under vacuum at 60° C. for 48 hours to give 28.535 g of poly(MCPMA/OTDA/HADA) (50/30/20) copolymer (MP-2) (Mw=13,474 and Mw/Mn=1.64).

Example 3: Synthesis of Poly(MCPMA/OTDA) (MP-3)

Monomers of MCPMA (17.234 g), and OTDA (22.766 g) were dissolved in 60 g of PGMEA. The monomer solution was degassed by bubbling with nitrogen for 20 min PGMEA (30.837 g) was charged into a 500 mL three-neck flask equipped with a condenser and a mechanical stirrer and was degassed by bubbling with nitrogen for 20 min Subsequently the solvent in the reaction flask was brought to a temperature of 80° C. V601 (dimethyl-2,2-azodiisobutyrate) (2.359 g) was dissolved in 8 g of PGMEA and the initiator solution was degassed by bubbling with nitrogen for 20 min. The initiator solution was added into the reaction flask and then monomer solution was fed into the reactor dropwise over the 3 hour period under rigorous stirring and nitrogen environment. After monomer feeding was complete, the polymerization mixture was left standing for one additional hour at 80° C. After a total of 4 hours of polymerization time (3 hours of feeding and 1 hour of post-feeding stirring), the polymerization mixture was allowed to cool down to room temperature. Precipitation was carried out MTBE (1694 g). The power precipitated was collected by filtration, air-dried overnight, re-dissolved in 120 g of THF, and re-precipitated into MTBE (1694 g). The final polymer was filtered, air-dried overnight and further dried under vacuum at 60° C. for 48 hours to give 33.058 g of poly(MCPMA/OTDA) (50/50) copolymer (MP-3) (Mw=13,109 and Mw/Mn=1.80).

37

Example 4: Synthesis of Monomer A

Scheme: Monomer A

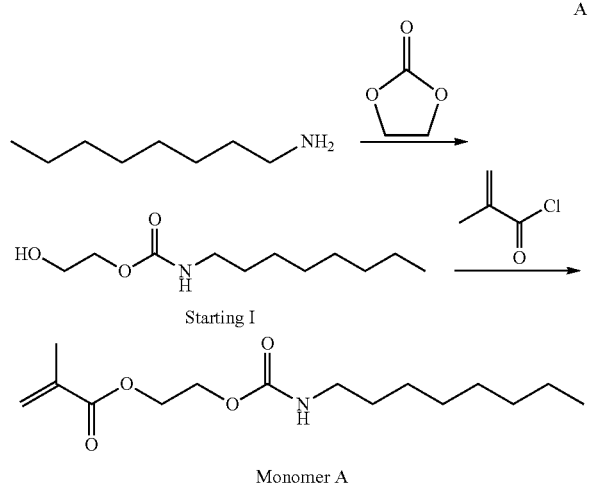

n-Octylamine (10.0 g, 0.07743 mol) and ethylene carbonate (6.883 g, 0.0782 mol) were charged into round-bottom flask. The mixture was stirred at 100° C. for 2 h. The reaction mixture was cooled to room temperature and filtered. The 16.3 g of product (Starting I) was obtained.

Starting I (10.0 g, 0.0461 mol) and triethylamine (19.24 mL, 0.138 mol) were dissolved in 100 mL of dry methylene chloride into round-bottom flask under nitrogen atmosphere. Methacryloyl chloride (5.82 mL, 0.0599 mol) was added dropwisely at 0° C. The reaction mixture was slowly warmed up to room temperature and allowed to stir at this temperature for 3 h.

The reaction mixture was transferred to 100 mL of deionized water and the organic phase was washed with an aqueous NH₄Cl and deionized water consecutively. The collected organic solution was dried over sodium sulfate, filtered and concentrated in vacuo. The 11.3 g of product (Monomer A as depicted I above Scheme) was obtained.

Example 5: Synthesis of Monomer B

Scheme: Monomer B

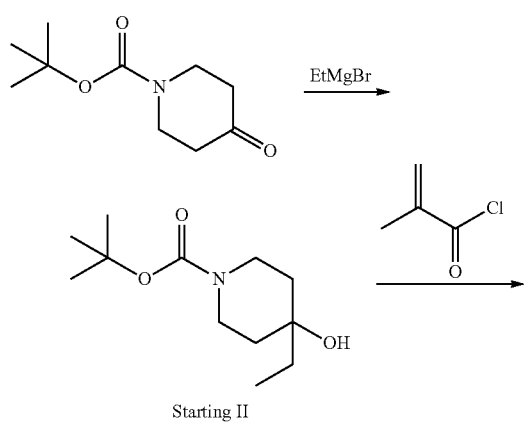

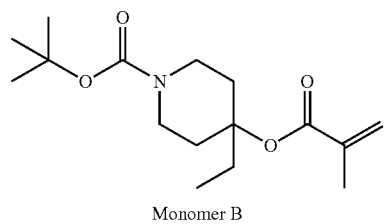

Monomer B 1-(tert-Butoxycarbonyl)-4-piperidone (15.00 g, 0.0753 mmol) were dissolved in 300 mL of diethyl ether into round-bottom flask under nitrogen atmosphere. The resulting solution was cooled to −40° C. and 3 M solution of ethyl magnesium bromide (32.64 mL, 0.0979 mmol) in diethyl ether was added. The reaction was allowed to stir at −30~−40° C. for 30 min, then slowly warmed up to room temperature and stirred an additional 6 h. The reaction was quenched by slow addition of H₂O and the resulting mixture was transferred to 200 mL of deionized water and the organic phase was washed with saturated NH₄Cl. and the organic phase was washed with saturated NH₄Cl and deionized water consecutively, The collected organic solution was dried over sodium sulfate, filtered and concentrated in vacuo. The 12.2 g of product (Starting II) was obtained.

Starting II (shown in the above Scheme—0.0 g, 0.0436 mol) and triethylamine (18.23 mL, 0.131 mol) were dissolved in 100 mL of methylene chloride into round-bottom flask under nitrogen atmosphere. Methacryloyl chloride (5.5 mL, 0.0567 mol) was added dropwisely at 0° C. The reaction mixture was slowly warmed up to room temperature and allowed to stir at this temperature for 3 h.

The reaction mixture was transferred to 100 mL of deionized water and the organic phase was washed with an aqueous NH₄Cl and deionized water consecutively. The collected organic solution was dried over sodium sulfate, filtered and concentrated in vacuo. The 9.6 g of product TBPEMA (Monomer B as shown in the above) was obtained.

Example 6: Synthesis of Polymer B

Scheme: Polymer B

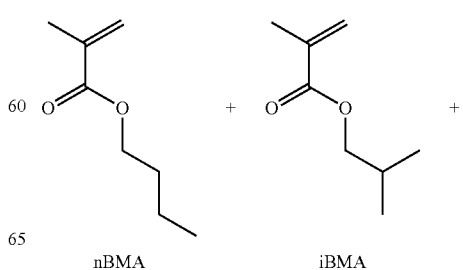

nBMA       iBMA

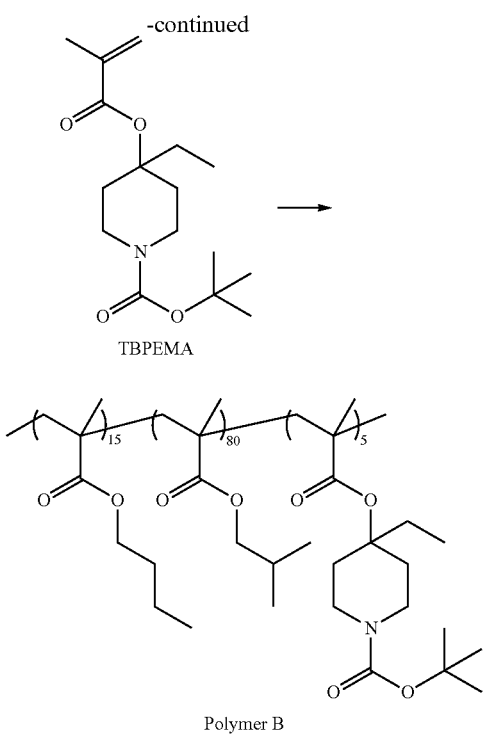

TBPEMA

Polymer B

A series of monomers, nBMA (2.85 g) (n-butyl methacrylate), iBMA (15.17 g) (iso-butyl methacrylate) and of TBPEMA (1.98 g) were dissolved in 16.333 g of PGMEA in round-bottom flask at room temperature with stirring and degassed with nitrogen for 20 min PGMEA (30.333 g) was charged into a Julabo reactor equipped with a condenser and a mechanical stirrer. After degassed with nitrogen for 20 min. The solvent in the Julabo reactor was heated up to 80° C. In other round-bottom flask, the initiator V601 (3.64 g) was dissolved in 5.47 g of PGMEA and degassed with nitrogen for 20 min. The initiator solution was added slowly into the Julabo reactor and stirred for 15 min the monomer solution was fed into the Julabo reactor dropwisely over the 3 hours with rigorous stirring under nitrogen environment. After monomer feeding was completed, the reaction mixture was stirred for an hour at 80° C. The reaction mixture was allowed to cool down to room temperature to methanol and water solvent mixture (865 g) with 8 to 2 ratios. The precipitated polymer was collected by filtration and dried in air overnightly. The dried polymer was re-dissolved in 46.7 g of THF and re-precipitated in methanol and water solvent mixtures (667 g) with 8 to 2 ratios. The final polymer was filtered, and dried in air overnight and under vacuum at 50° C. for 24 hours to give 12.4 g of poly(nBMA/iBMA/TBPMA) (14.7/80.8/4.5) Polymer B shown in the above Scheme (Mw=5690 and PDI=1.42).

Example 7: Preparation of Sample A Overcoat Composition

An overcoat composition of the invention is prepared by admixing the following components, 5.14 g polymer-B solution (20%) in IBIB, 2.21 g Quencher-A solution (1%) in IBIB and 92.7 g IBIB and then this mixture was filtered with a 0.2 micron Nylon filter.

Polymer B:

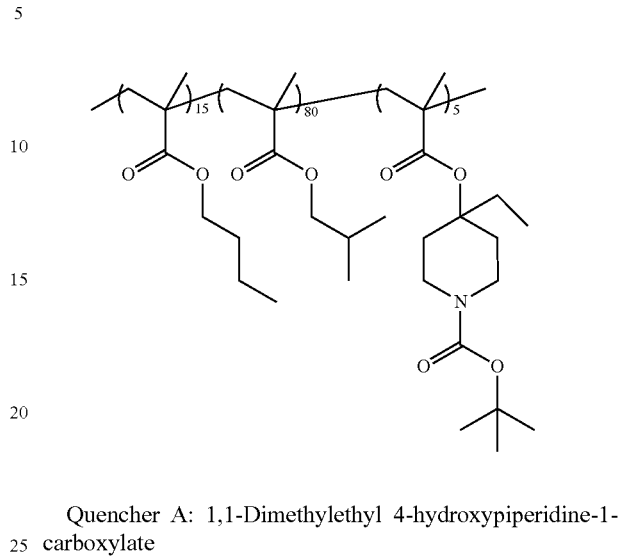

Quencher A: 1,1-Dimethylethyl 4-hydroxypiperidine-1-carboxylate

Example 8: Preparation of Sample B Photoresist Composition

A photoresist composition is prepared by admixing the following components, 17.73 g polymer-D solution (15%) in PGMEA, 16.312 g PAG-A solution (1%) in methyl-2-hydroxyisobutyrate, 3.463 g PAG-B solution (1%) in PGMEA, 6.986 g WPAG solution (2%) in methyl-2-hydroxyisobutyrate, 4.185 g Quencher-B solution (1%) in PGMEA, 0.248 g EBL (25%) in PGMEA, 25.63 g PGMEA, 9.69 g gamma-butyrolactone and 22.61 g methyl-2-hydroxyisobutyrate and then this mixture was filtered with a 0.2 micron Nylon filter.

Polymer-D:

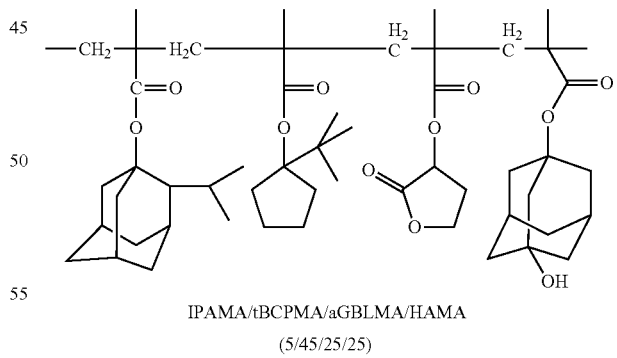

IPAMA/tBCPMA/aGBLMA/HAMA
(5/45/25/25)

PAG-A: Triphenylsulfonium [(adamantan-1-yl)methyl]oxycarbonyl difluoromethanesulfonate PAG-B: Sulfonium, triphenyl-, salt with 1,1,2,2,3,3,4,4,4-nonafluoro-1-butanesulfonic acid WPAG: tri-p-tolylsulfonium ((3s,5s,7s)-adamantan-1-yl) sulfamate Quencher-B: N,N-dioctyl-1-Octanamine,

EBL:

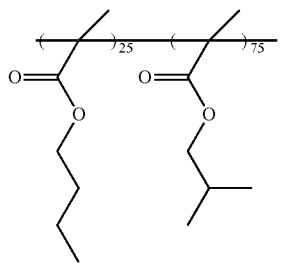 [SMILES: CCCCOC(=O)C(C)(C)CC(C)(C)C(=O)OCC(C)C]

Example 9: Immersion Lithography 300 mm HMDS-primed silicon wafers were spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C., providing the first BARC layer thickness of 900 Å.

The topcoat composition of Example 8 is spin coated onto a silicon wafer having a coating layer of the photoresist composition of Example 8.

The fabricated films were then exposed through a mask on Nikon S306C ArF immersion scanner using the illumination conditions as follows: 1.3 NA, Annular with XY-polarization, δ0.64-0.8. The exposure dose was varied from 23.0 mJ/cm² to 47.0 mJ/cm² by 1 mJ/cm². The exposed film was then post-exposure baked at 90° C. for 60 seconds, followed by the developing with n-butyl acetate for 18 seconds using a TEL CLEAN TRAC LITHIUS i+, which provides the patterns with negative tone development. Critical dimensions (CDs) of the patterns of interests (50 nm 1:3 Contact hole, 168 nm pitch, bright field phase-shifted by 180° with transmittance 0.06) were measured on a Hitachi CG4000 CD SEM.

Example 10: Immersion Lithography

The topcoat composition of Example 7 is spin coated onto a silicon wafer having a coating layer of a Negative Tone Developable (NTD) photoresist. The NTD photoresist of Example 8 contains a first polymer with photoacid-labile groups, a photoacid generator compound, an amine quencher compound, a second polymer that is a fluorinated resin and solvent. The first polymer is a copolymer of isoproyladamantyl methacrylate/isopropylcyclopropyl methacrylate/γ-butyrolactone methacrylate/hydroxyadamantyl methacrylate (20/25/30/25). The photoresist photoacid generator compound is triphenylsulfonium perfluorobutylsulfonate present in an amount of 6.0 weight % based on total solids (all photoresist materials except solvent). The photoresist quencher compound is trioctyl amine present in an amount of 1.3 weight % based on total solids. The photoresist solvent is propyleneglycolmonomethylether acetate/methyl-2-hydroxyisobutyrate at 50:50 relative volume percent.

The topcoat coated photoresist layer is imaged in an immersion lithography system with patterned radiation having a wavelength of 193 nm. The exposed wafers are post-exposure baked at 90° C. for 60 seconds and then developed using n-butyl acetate developer for approximately 30 seconds to give negative tone patterns of resist with overcoated topcoat composition.

Example 11: Comparative Evaluation Results

It was found that improved lithographic process windows were achieved with use of the present topcoat composition as compared with the same photoresist composition where no topcoat composition was utilized. Results are shown in Table 2 below.

300 mm silicon wafers were spin-coated with AR™ 40A antireflectant (Rohm and Haas Electronic Materials) to form a first BARC layer on a TEL CLEAN TRAC LITHIUS i+ coater/developer. The wafers were baked for 60 seconds in excess of 200° C. Photoresist compositions as specified in Table 2 below were then coated on the dual BARC-coated wafers and soft-baked at 90° C. for 60 seconds on a TEL CLEAN TRACK LITHIUS i+ coater/developer. A topcoat composition as specified in Table 2 below was coated on top of the resist and soft-baked to remove solvent.

Negative Tone Development Process

Wafers were exposed through a mask on a Nikon S610C immersion scanner using an annular illumination with L30 NA, 0.8 outer sigma, 0.6 inner sigma and XY polarization. The exposed wafers were post-exposure baked at 90° C. for 60 seconds and then developed using a n-butyl acetate for 25 seconds on a TEL CLEAN TRACK™ LITHIUS™ i+ coater/developer to give negative tone patterns. Optimum energy ($E_{op}$) to print holes of dimensions set forth in Table 1 below was determined for the single exposure NTD process by plotting CD values, measured on a Hitachi 004000 CD SEM, as a function of exposure energy using a mask CD at 65 nm (the diameter of an opaque post on the mask) and a pitch CD at 96 nm (a mask CD plus the distance between opaque posts). Exposure latitude (EL) was measured. EL is defined by the CD change (ΔCD) per exposure energy (mJ/cm²) within ±10% of a target CD (CD) according to the following formula: EL=(1.1×$CD_t$–0.9×CD)/(Eop of 1.1×$CD_t$–Eop of 0.9×$CD_t$). Focus latitude (FL in Table 1 below) was determined as the change in focus needed to effect a ±10% change in linewidth. Focus offset was changed in an increment of 20 nm to examine depth of focus (DOF) for different examples and DOF was determined by the hole fidelity from SEM images taken through the focus change.

Results are shown in Table 1 below.

TABLE 1

| Litho Evaluation | | Sample B photo resist | Sample A overcoat on Sample B photo resist |
|---|---|---|---|
| 52 nm 96 pitch | Eop | 56.1 mj | 56.5 mj |
| | EL (%) | 7.40% | 9.50% |
| | FL | 146.7 nm | 200.0 nm |
| 50 nm 168 pitch | Eop | 62.1 mj | 63.4 mj |
| | EL (%) | 9.90% | 10.20% |
| | FL | 101.5 nm | 120.0 nm |
| 50 nm 600 pitch | Eop | 55.8 mj | 57.5 mj |
| | EL (%) | 7.30% | 7.30% |
| | FL | 50.0 nm | 80.4 nm |

What is claimed is:
1. A composition suitable for use in forming a layer over photoresist layer, the composition comprising:
   a first polymer comprising:
      first units comprising a reactive sulfamate moiety spaced from the polymer backbone, wherein the sulfamate moiety produces a basic cleavage product during lithographic processing of the photoresist composition, and wherein an acid-labile group is interposed between the first polymer backbone and the reactive sulfamate moiety.

2. A composition of claim 1 wherein the first polymer further comprises second units distinct from the first units, the second units each comprising 1) a reactive sulfamate moiety and 2) an acid-labile group.

3. A composition of claim 1 wherein the sulfamate moiety is spaced from the polymer by optionally substituted alkylene, optionally substituted carbon alicyclic, optionally substituted heteroalicyclic, optionally substituted carbocyclic aryl or optionally substituted heteroaryl.

4. A composition of claim 1 wherein the first polymer further comprises:
   third units that 1) comprise one or more hydrophobic groups and 2) are distinct from both of the first and second units.

5. A method for processing a photoresist composition, comprising:
   (a) applying a layer of a photoresist composition on a substrate;
   (b) above the photoresist composition layer, applying a layer of a composition of claim 1 to form a topcoat layer;
   (c) patternwise exposing the topcoat layer and photoresist layer to activating radiation; and
   (d) developing the exposed photoresist composition layer to provide a photoresist relief image.

6. The method of claim 5 wherein the exposed photoresist and topcoat layers are developed with an organic solvent composition that selectively removes unexposed portions of the photoresist composition layer to provide the photoresist relief image.

7. The composition of claim 1 wherein the composition does not contain an acid generator compound.

8. A coated substrate, comprising:
   (a) a substrate having a photoresist composition layer thereon; and
   (b) above the photoresist composition layer, a layer of a composition comprising:
   a first polymer comprising:
   first units comprising a reactive sulfamate moiety spaced from the polymer backbone, wherein the sulfamate moiety produces a basic cleavage product during lithographic processing of the photoresist composition, and wherein an acid-labile group is interposed between the first polymer backbone and the reactive sulfamate moiety.

* * * * *